(12) United States Patent
Novakovic et al.

(10) Patent No.: US 12,146,035 B2
(45) Date of Patent: Nov. 19, 2024

(54) OSCILLATORY GELS

(71) Applicant: UNIVERSITY OF NEWCASTLE UPON TYNE, Tyne and Wear (GB)

(72) Inventors: Katarina Novakovic, Tyne and Wear (GB); Anna Isakova, Tyne and Wear (GB)

(73) Assignee: University of Newcastle Upon Tyne, Tyne and Wear (GB)

( * ) Notice: Subject to any disclaimer, the term of this patent is extended or adjusted under 35 U.S.C. 154(b) by 889 days.

(21) Appl. No.: 17/253,577

(22) PCT Filed: Jun. 26, 2019

(86) PCT No.: PCT/GB2019/051798
§ 371 (c)(1),
(2) Date: Dec. 17, 2020

(87) PCT Pub. No.: WO2020/002909
PCT Pub. Date: Jan. 2, 2020

(65) Prior Publication Data
US 2021/0277190 A1 Sep. 9, 2021

(30) Foreign Application Priority Data

Jun. 27, 2018 (GB) ...................................... 1810523

(51) Int. Cl.
*C08J 3/075* (2006.01)
*B01J 31/06* (2006.01)

(52) U.S. Cl.
CPC ............ *C08J 3/075* (2013.01); *B01J 31/063* (2013.01); *B01J 2231/70* (2013.01); *B01J 2531/824* (2013.01); *B01J 2531/845* (2013.01)

(58) Field of Classification Search
CPC . B01J 31/063; B01J 2231/70; B01J 2531/824
See application file for complete search history.

(56) References Cited

U.S. PATENT DOCUMENTS

| | | | |
|---|---|---|---|
| 6,068,853 A * | 5/2000 | Giannos | A61K 9/7084 |
| | | | 604/890.1 |
| 8,158,002 B1 | 4/2012 | Lupton et al. | |
| 9,944,729 B2 * | 4/2018 | Meyer | C08J 3/075 |

FOREIGN PATENT DOCUMENTS

| | | |
|---|---|---|
| JP | H08-40987 A | 2/1996 |
| JP | 2009-108769 A | 5/2006 |
| JP | 2006-343650 A | 12/2006 |
| JP | 2010-222465 A | 10/2010 |
| JP | 2014-176931 A | 9/2014 |
| JP | 2014-210260 A | 11/2014 |
| JP | 2014-210915 A | 11/2014 |
| JP | 2014-212685 A | 11/2014 |

OTHER PUBLICATIONS

Yoshida, R. "Self-Oscillating Polymer Gels as Novel Biomimetic Materials" 35th Annual International Conference of the IEEE EMBS, 2013, pp. 318-321 (Year: 2013).*
Yoshida, R. "Self-Oscillating Polymer Gels as Novel Biomimetic Materials" 35th Annual International Conference of the IEEE EMBS, Osaka, Japan, Jul. 3-7, 2013 (Year: 2013).*
Isakova, A. et al. "Oscillatory chemical reactions in the quest for rhythmic motion of smart materials" European Polymer Journal 95 (2017) 430-439 (Year: 2017).*
Malashkevich,A.V.etal.NewOscillatingReactioninCatalysisbyMetal Complexes:AMechanismofAlkyneOxidativeCarbonylation.J. Phys. Chem.A,vol. 101,No. 51,1997 (Year: 1997).*
Hidaka, M. et al. "Self-oscillating gel composed of thermosensitive polymer exhibiting higher LCST" Journal of Controlled Release 150 (2011) 171-176 (Year: 2011).*
Yoshida, R., "A Self-Oscillating Gel That Beats Like a Heart Muscle," The Biophysical Society of Japan 51(6):264-267, Nov. 29, 2011.
Yoshida, R., "Self-Oscillating Gel—Gel With Temporal Structure," Society of Polymer Science 54(7):466-469, 2023.
Yoshida, R., "Self-Oscillating Polymer and Gels as Novel Biomimetic Materials, " Bulletin of the Chemical Society of Japan 81(6):676-688, 2008.
Japanese Office Action dated Mar. 8, 2023, issued in Japanese Patent Application No. 2020-571840, filed Dec. 23, 2020, 21 pages.
hidaka et al., "Self-oscillating gel composed of thermosensitive polymer exhibiting higher LCST," Journal of Controlled Release, 2011, 150: 171-176.
Imyanitov, "Dialectics and synergetic in chemistry. Periodic Table and oxcillating reactions," Found Chem, 2016, 18:21-56.
Isakova et al., "Oscillatory chemical reactions in the quest for rhythmic motion of smart materials," European Polymer Journal, 2017, 95:430-439.
Ryo, "Self-Oscillating Polymer Gels as Novel Biomimetic Materials," 35th Annual International Conferencce of the IEEE EMBS, 2013, pp. 318-321.
Search Report under Section 17(5), dated Dec. 21, 2018, received in G.B. Application No. 1810523.9.
International Search Report and Written Opinion, dated Oct. 30, 2019, received in International Application No. PCT/GB2019/05198.

* cited by examiner

*Primary Examiner* — Andrew S Rosenthal
(74) *Attorney, Agent, or Firm* — Barry L. Davison; Davis Wright Tremaine LLP

(57) ABSTRACT

This invention relates to gels that undergo either oscillatory stepwise expansion or oscillatory expansion and contraction. An oscillatory reaction occurs within the gel, changing the conditions of the gel, and causing the gel to expand and optionally contract. The gels may be used for oscillatory release of a chemical agent.

24 Claims, 13 Drawing Sheets

OSCILLATORY GELS

CROSS-REFERENCE TO RELATED APPLICATIONS

The present application is a U.S. National Stage entry under 35 U.S.C. § 371 of International Application No. PCT/GB2019/051798, filed on Jun. 26, 2019, designating the United States of America and published in English on Jan. 2, 2020, which in turn claims priority to G.B. Application No. 1810523.9, filed on Jun. 27, 2018, each of which is hereby incorporated by reference in its entirety.

This invention relates to gels that undergo either oscillatory stepwise expansion or oscillatory expansion and contraction. An oscillatory reaction occurs within the gel, changing the conditions of the gel, and causing the gel to expand and optionally contract. The gels may be used for oscillatory release of a chemical agent.

BACKGROUND

The oscillatory expansion and contraction of a gel could be a powerful tool in a range of industries, including medical applications such as wound healing and, if the expansion is accompanied by release of a drug entity, chronopharmacotherapy.

BRIEF SUMMARY OF THE DISCLOSURE

In accordance with the present invention there is provided a gel that undergoes oscillatory expansion; said gel comprising:
  a polymeric solid phase that expands in response to a non-physical stimulus;
  a transition metal catalyst bound to a component of the polymeric solid phase; and
  an organic compound;
wherein the catalyst catalyses a sustained oscillatory reaction of the organic compound, said oscillatory reaction providing said non-physical stimulus to the gel and causing the gel to undergo oscillatory expansion; and wherein the oscillatory reaction is sustained without any further catalyst being added.

The oscillatory reaction changes the conditions to which the gel is exposed and in so doing drives the oscillatory expansion of the gel.

The gel may undergo oscillatory stepwise expansion. Thus, it may be that the gel expands in steps. Stepwise expansion can be thought of as arising because the rate of expansion is oscillatory (i.e. relatively fast expansion, then a period in which the rate of expansion decreases, then a period of relatively little or no expansion, then a period in which the rate of expansion increases etc.). Thus, the gel may oscillate between periods of relatively rapid expansion and periods of no expansion or slow expansion. In these embodiments, the gel will not revert to its original size between periods of expansion. This will typically occur in response to a change in conditions (the non-physical stimulus) that has an oscillatory rate of change. As illustrative examples, the gel may expand in response to an increase in pH that has an oscillatory rate of change (oscillating between periods of relatively rapid increase in pH and periods of no increase or slow increase in pH) or the gel may expand in response to a decrease in pH that has an oscillatory rate of change (oscillating between periods of relatively rapid decrease in pH and periods of no decrease or slow increase in pH)

The gel may undergo oscillatory expansion and contraction. Thus, the gel alternates between periods of expansion and periods of contraction. Where the gel undergoes oscillatory expansion and contraction, the contraction will typically occur in response to a second non-physical stimulus that is the opposite of the non-physical stimulus that causes the gel to expand (the first non-physical stimulus). This will typically occur in response to a change of conditions that is itself oscillatory. As illustrative examples: the gel may alternate between a period of expansion in response to an increase in pH and a period of contraction in response to a decrease in pH; the gel may alternate between a period of expansion in response to a decrease in pH and a period of contraction in response to an increase in pH; the gel may alternate between a period of expansion in response to the release of heat from the reaction and a period of contraction as the gel cools; the gel may alternate between a period of expansion in response to an increase in redox potential and a period of contraction in response to a decrease in redox potential; or the gel may alternate between a period of expansion in response to a decrease in redox potential and a period of contraction in response to an increase in redox potential.

Gels that are suitable for use in the reaction include 'smart gels', gels that can expand and optionally contract in response to non-physical stimuli such as heat, pH changes or redox changes.

The gel may be biocompatible, i.e. it may comprise a biocompatible polymeric solid phase.

Suitable solid phases include those based on chitosan. The chitosan solid phase may be formed of chitosan that has been modified to incorporate binding sites for the transition metal. Alternatively, the chitosan solid phase may be formed of chitosan throughout which is interspersed a polymer that incorporates binding sites for the transition metal (e.g. chitosan that has been modified to incorporate binding sites for the transition metal). Suitable binding sites for a transition metal may include those having two atoms selected from oxygen, nitrogen and phosphorous separated by from two to 4 carbon atoms, e.g. heteroaryl imines, prolineamides, heteroaryl-triazoles. The chitosan may be cross-linked, e.g. with a dialdehyde. An illustrative cross-linking agent is genipin. Chitosan based gels will typically expand in response to a decrease in pH.

Alternatively, the solid phase may be formed of a synthetic polymer. The solid phase may be formed of a synthetic polyacrylate.

Illustrative gels that would be suitable include: poly(N-isopropylacrylamide) (polyNIPAM), poly[2-(dimethylamino)ethyl methacrylate] (polyDMAEMA), and hydroxypropylcellulose. These gels typically expand in response to a change in temperature.

Further illustrative gels include: poly[2-(dimethylamino) ethylacrylate], poly[2-(diethylamino) ethylacrylate], poly[2-(diisopropylamino) ethylacrylate], polysulfonates and polyphosphonates. These gels typically expand in response to a change in pH.

The polymer (e.g. the synthetic polyacrylate) may incorporate amine groups. Amine groups can cause the gel to expand in response to a decrease in pH.

The polymer (e.g. the synthetic polymer) may incorporate PEG groups. PEG groups can increase the hydrophilicity of a gel, potentially increasing its biocompatibility.

The synthetic polymer may incorporate amine groups and PEG groups. The polymer solid phase may comprise cross-linking groups, e.g. diacrylates in the case of polyacrylates.

The polymers that make up the polymeric solid phase may comprise PEG groups.

The transition metal catalyst is bound to a component of the polymeric solid phase. It may be that the catalyst is bound to the gel forming polymer. Alternatively, it may be that the catalyst is bound to a polymer that is interspersed within the gel forming polymer.

The transition metal catalyst may be distributed homogeneously through the gel. Alternatively, the gel may comprise areas of higher concentration of the transition metal catalyst and areas of lower concentration of the transition metal catalyst.

The transition metal catalyst may comprise a metal selected from Pd, Pt, Fe, Cu, Co, Ru, Rh and Ir. The transition metal catalyst may comprise palladium. The transition metal catalyst may comprise $Pd^{2+}$, e.g. $PdCl_2$. The transition metal catalyst may comprise cobalt. The transition metal catalyst may comprise $cobalt^{2+}$, e.g. $Co(NO_3)_2 \cdot 6H_2O$.

The catalyst may be selected such that, under the conditions of the oscillatory reaction, regeneration of the catalyst is autocatalytic. Autocatalytic means that reacted catalyst can only be regenerated in the present of unreacted catalyst.

It may be that the organic compound is bound (e.g. covalently attached) to a component of the polymeric solid phase. It may be that the organic compound is bound (e.g. covalently attached) to the gel-forming polymer. Alternatively, it may be that the organic compound is bound (e.g. covalently attached) to a polymer that is interspersed within the gel forming polymer. Binding the organic compound to a component of the polymeric solid phase means that the organic compound and the products of the reaction are not released by the gel.

Alternatively, it may be that the organic compound is a component of the liquid phase of the gel.

The organic compound may be distributed homogeneously through the gel. This may be the case whether the organic compound is a component of the liquid phase of the gel or whether the organic compound is bound to a component of the polymeric solid phase.

Alternatively, the gel may comprise areas of higher concentration of the organic compound and areas of lower concentration of the organic compound. This will typically be the case where the organic compound is bound to a polymer that is interspersed within the gel forming polymer.

Where both the transition metal catalyst and the organic compound are bound to a polymer that is interspersed within the gel forming polymer, they may be both bound to the same polymer or they may each be bound to different polymers. Where there are areas of higher concentration of the organic compound and areas of lower concentration of the organic compound and there are also of higher concentration of the transition metal catalyst and areas of lower concentration of the transition metal catalyst, it may be that the areas of higher concentration of the organic compound are also areas of higher concentration of the transition metal catalyst. This is most efficiently achieved by having both the organic compound and the transition metal catalyst incorporated into the same polymer. The polymer to which the transition metal and or the organic compound are bound may further incorporate PEG groups.

The organic compound may comprise a functional group suitable for undergoing catalytic reaction with a transition metal. Illustrative examples include alkyne groups, alkene groups, aryl halide groups and aryl boronate or boronic acid groups. It may be that the organic compound comprises at least one alkyne or alkene. It may be that the organic compound comprises more than one alkyne or more than one alkene. It may that the organic compound comprises at least one alkyne. It may that the organic compound comprises more than one alkyne.

The oscillatory reaction may be a palladium-catalysed oxidative carbonylation (PCOC) reaction. In such reactions, the transition metal catalyst is a $Pd^{2+}$ catalyst and the organic compound is an alkyne. The oscillatory reaction may be a cobalt-catalysed oxidative carbonylation reaction, e.g. a cobalt-catalysed oxidative carbonylation reaction. In such reactions, the transition metal catalyst is a $CO^{2+}$ catalyst and the organic compound is an alkyne. The alkyne reacts with carbon monoxide and an organic alcohol. An illustrative PCOC reaction is below:

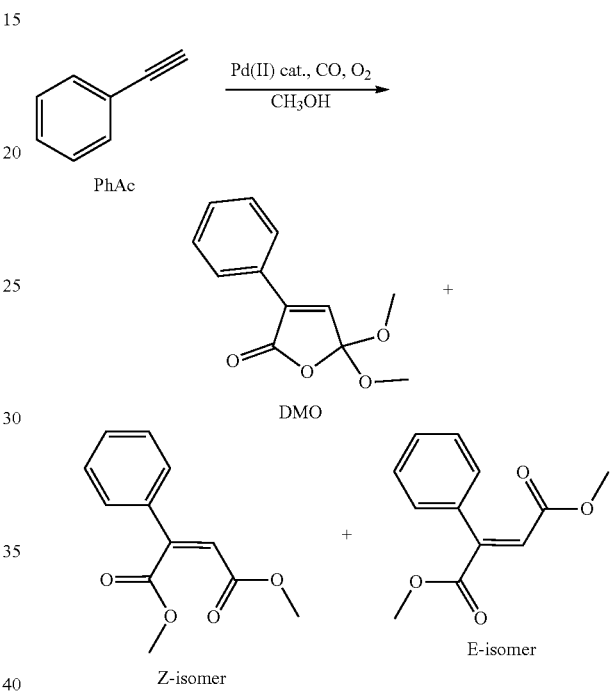

The oscillatory reaction may be an oxidative Heck reaction. An illustrative oxidative Heck reaction is below:

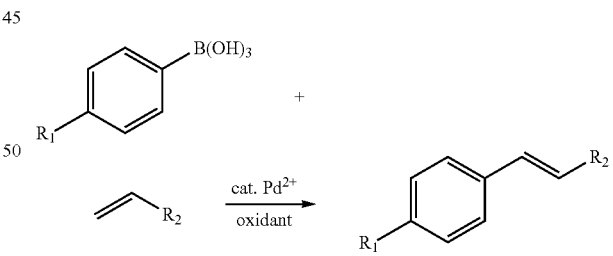

In the oxidative heck reaction, it may be that the boronic acid is bound to (e.g. covalently attached to) a component of the polymeric solid phase. It may be that the alkene is bound to (e.g. covalently attached to) a component of the polymeric solid phase. It may be that both the boronic acid and the alkene are bound to (e.g. covalently attached to) a component of the polymeric solid phase.

The liquid phase of the gel will typically comprise an organic alcohol, e.g. a $C_1$-$C_{10}$-alkylalcohol. The solvent may comprise a $C_1$-$C_4$-alkylalcohol, e.g. methanol, ethanol or isopropanol. This will particularly be the case where the oscillatory reaction is a PCOC reaction.

The liquid phase of the gel may comprise water. In certain specific embodiments, when the liquid phase comprises water this can give rise to stepwise oscillatory expansion.

The gel (e.g. the liquid phase) may incorporate one or more further reactants in the oscillatory reaction. Alternatively, the gel may encapsulate a reservoir within which one or more further reactants in the oscillatory reaction is retained. Where the oscillatory reaction is a PCOC reaction, the further reactant in the oscillatory reaction is carbon monoxide or a source of carbon monoxide. Examples include formates, (e.g. phenylformate, pyridinyl methyl formate), formamides (e.g. formanilide) or metal carbonyls (e.g. $Ru_3(CO)_{12}$ or $Fe(CO)_5$]).

The oscillatory reaction may be sustained for longer than 1 hour. The oscillatory reaction may be sustained for longer than 24 hours. The oscillatory reaction may be sustained for longer than 48 hours. The oscillatory reaction may be sustained for longer than 7 days. The oscillatory reaction may be sustained for longer than 28 days. The inventors have observed that PCOC reactions can last without replenishment of the catalyst or the alkyne for longer than 28 days. It is believed that no prior art oscillatory reactions last for longer than a few minutes.

It may be that the oscillatory or stepwise expansion of the gel causes oscillatory release of an agent from the gel. It may be that the gel further comprises the agent. Alternatively, the gel may encapsulate a reservoir within which the agent is retained. As mentioned above, one or more further reactants in the oscillatory reaction are also present in the reservoir.

The agent will typically be an organic compound. The agent will typically be an organic compound that does not react under the conditions of the oscillatory reaction. The agent may be a drug molecule. The agent may be a drug molecule having a molecular weight below 1000 g/mol. The agent may be a drug molecule having a molecular weight below 500 g/mol. Alternatively, the agent may be a biopolymeric drug, e.g. a protein, an antibody or conjugate thereof, a polysaccharide, a polynucleotide. Exemplary drugs that might be released include those that are used to treat a disease selected from arthritis, diabetes, asthma, cardiovascular disorders, etc.

In a second aspect of the invention is provided a method of causing oscillatory expansion and contraction of a gel, the method comprising either:
- A) providing a gel of the first aspect with one or more chemicals that react with the organic compound in the oscillatory reaction catalysed by the catalyst and/or an initiator; or
- B) providing a gel as described in the first aspect but not comprising the organic compound, with the organic compound and optionally one or more chemicals that react with the organic compound in the oscillatory reaction catalysed by the catalyst and/or an initiator.

Where the oscillatory expansion of the gel causes oscillatory release of an agent from the gel, the method of the second aspect is a method of causing oscillatory release of an agent from the gel, the method comprising either:
- A) providing a gel of the first aspect with one or more chemicals that react with the organic compound in the oscillatory reaction catalysed by the catalyst and/or an initiator; or
- B) providing a gel as described in the first aspect but not comprising the organic compound, with the organic compound and optionally one or more chemicals that react with the organic compound in the oscillatory reaction catalysed by the catalyst and/or an initiator.

Option B) above may be the case where the organic compound is not bound to a component of the polymeric solid phase.

It may be that the method does not comprise the addition of further catalyst or organic compound to the gel. The inventors have found that the current invention can provide oscillatory reactions that are sustained for long periods of time without replenishment of the catalyst or the organic compound.

In the PCOC reaction, for example, the method may comprise providing the gel with CO and/or an alcohol. Optionally, an initiator may also be added.

The initiator may be HI.

BRIEF DESCRIPTION OF THE DRAWINGS

Embodiments of the invention are further described hereinafter with reference to the accompanying drawings, in which.

DETAILED DESCRIPTION

Figure 1:
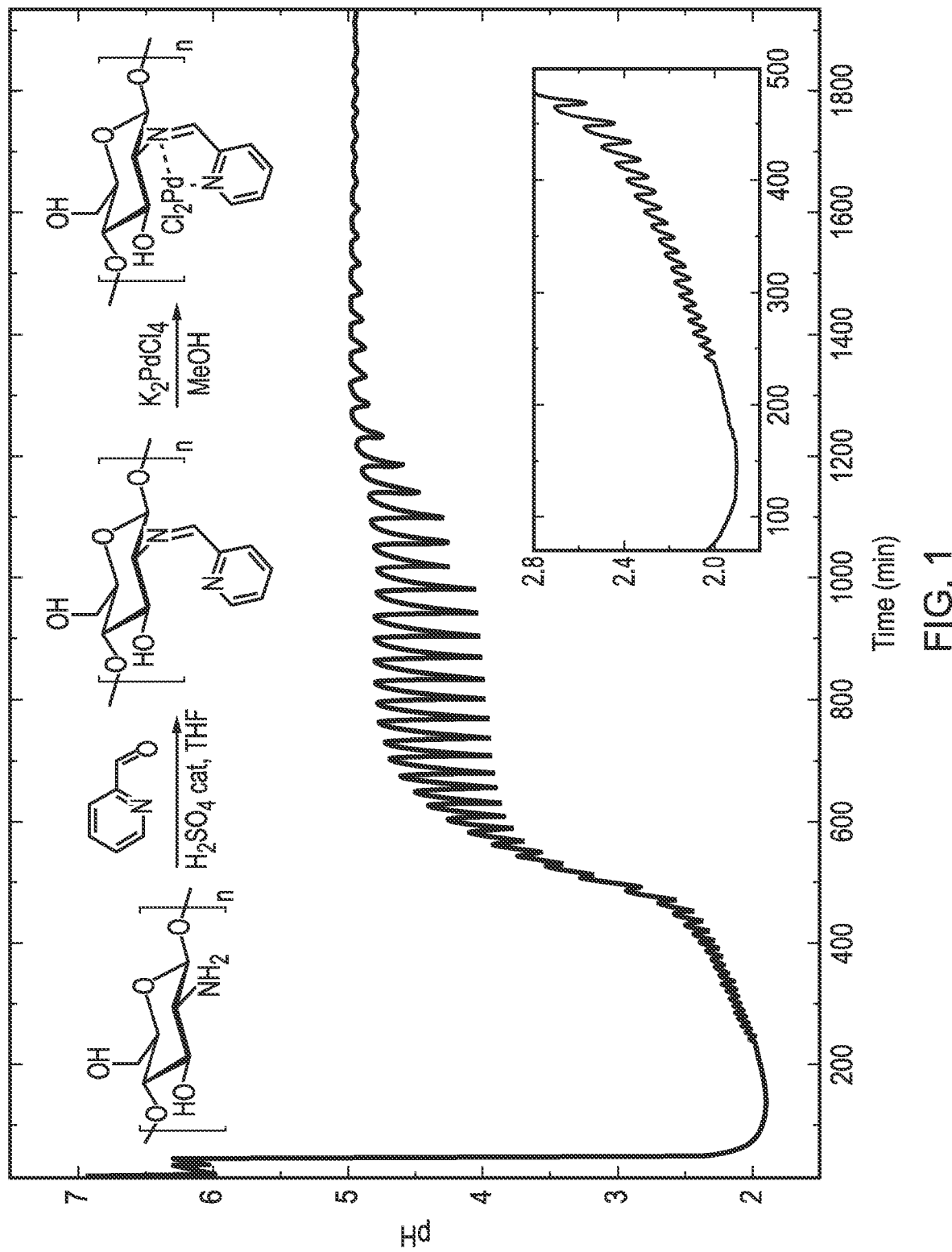
FIG. 1 shows a scheme of synthesis of a chitosan-based palladium catalyst (Chi-IM-$PdCl_2$). Oscillations in pH recorded in the oxidative carbonylation of phenylacetylene in methanol at 20° C. using Chi-IM-$PdCl_2$ as a catalyst. Inset shows the start of oscillations at 244 min.

Throughout this specification, the term 'oscillatory' is intended to mean repetitive variation in a property over time, i.e. alternation between periods of high or low values for said property. Examples of said property include (rate of release of an agent, size (i.e. degree of expansion) of gel, pH, temperature, rate of expansion, rate of pH change, rate of change of temperature, rate of reaction, rate of change of rate of reaction). It is not intended to mean a mathematically precise sinusoidal pattern, merely a repeated alternation between a relative peak and a relative trough for said property. A gel comprises a solid phase and a liquid phase. The liquid phase is distributed throughout the solid phase.

The term 'non-physical stimulus' is intended to describe any change in the chemical or energetic conditions to which the gel is subjected. This change in conditions will be generated by the oscillatory reaction occurring within the gel. The term 'non-physical stimulus' intended to exclude the use of a solid object or externally applied pressure change to cause the gel to expand and contract. The non-physical stimulus may be a change in pH (e.g. an increase in pH or a decrease in pH). The non-physical stimulus may be a change in temperature (e.g. an increase in temperature). The non-physical stimulus may be a change in redox potential (e.g. an increase in redox potential or a decrease in redox potential).

The oscillatory reaction is sustained without any further catalyst being added. Sustained means that the oscillatory nature of the reaction (and the resultant effect, e.g. stepwise expansion or expansion and contraction of the gel or the release of agent) is continues over long periods of time (e.g. greater than 1 hour) without any need to add catalyst. Typically, the reaction will continue until substantially all of the organic compound has reacted. In this context, the term 'substantially all' may mean that greater than 50%, e.g. greater than 75% or greater than 90% of the organic compound has reacted. The oscillatory reaction will typically also be sustained without the need to add further organic compound. The reaction may be described as a batch-like reaction, at least with respect to the catalyst and the organic compound. It may be that a supply of other reactants, e.g. CO or alcohol, is available to the gel in order to sustain the oscillatory reaction.

An organic compound is a group of atoms that comprise carbon and hydrogen and that are covalently bonded together. The organic compound may also comprise one or more heteroatoms selected from oxygen, nitrogen, sulfur, phosphorous, halogen and boron. The organic compound may be covalently attached to a component of the polymeric solid phase. In this instance, the organic compound is a part of the larger macromolecule that comprises both the polymer chain and one or more of the groups of covalently bonded atoms that are herein referred to as the organic compound.

Biocompatible means that the gel does not stimulate a response or stimulates only a mild and/or transient response, as opposed to a severe or escalating response when the gel is placed or implanted into the human body.

The term 'bound' may mean attached via covalent bonding, ionic bonding, dative bonding, hydrogen bonding or Van der Waals forces. In the case of the organic molecule being bound to a component of the polymeric solid phase, the organic molecule is typically covalently attached to the component of the polymeric solid phase. In the case of the transition metal catalyst, the transition metal is typically bound to functional groups (e.g. bidentate ligands) that are covalently attached to the component of the polymeric solid phase. The metal is typically bound to said groups by dative bonding. The transition metal catalyst may also comprise other ligands that are bound to the transition metal but are not bound to the component of the polymeric solid phase, e.g. chloride ions or phosphate groups.

Throughout the description and claims of this specification, the words "comprise" and "contain" and variations of them mean "including but not limited to", and they are not intended to (and do not) exclude other moieties, additives, components, integers or steps. Throughout the description and claims of this specification, the singular encompasses the plural unless the context otherwise requires. In particular, where the indefinite article is used, the specification is to be understood as contemplating plurality as well as singularity, unless the context requires otherwise.

Features, integers, characteristics, compounds, chemical moieties or groups described in conjunction with a particular aspect, embodiment or example of the invention are to be understood to be applicable to any other aspect, embodiment or example described herein unless incompatible therewith. All of the features disclosed in this specification (including any accompanying claims, abstract and drawings), and/or all of the steps of any method or process so disclosed, may be combined in any combination, except combinations where at least some of such features and/or steps are mutually exclusive. The invention is not restricted to the details of any foregoing embodiments. The invention extends to any novel one, or any novel combination, of the features disclosed in this specification (including any accompanying claims, abstract and drawings), or to any novel one, or any novel combination, of the steps of any method or process so disclosed.

The reader's attention is directed to all papers and documents which are filed concurrently with or previous to this specification in connection with this application and which are open to public inspection with this specification, and the contents of all such papers and documents are incorporated herein by reference.

EXAMPLES

Example 1—Chitosan Imine Based System

In this Example, we demonstrate pulsatile release from chitosan-based macrogels which employ palladium-catalysed oxidative carbonylation (PCOC) reaction as a driving force of the oscillations within the smart chitosan macrogel.

A chitosan-based palladium catalyst is synthesised (denoted as Chi-IM-PdCl$_2$, FIG. 1), via imine chemistry, and used as prepared in the PCOC reaction, employing phenylacetylene as a substrate, in order to confirm that it generates oscillations (FIG. 1) (see below for synthesis, characterisation and experimental procedure). Chi-IM-PdCl$_2$ has physical appearance of black chitosan particles and swells in acidic environment (due to free amino groups on the chitosan), but does not dissolve due to the ability of palladium atoms to crosslink chitosan chains.

As can be seen in FIG. 1, oscillations in Chi-IM-PdCl$_2$ have a short induction period of only 244 min and continue for 1600 min until the substrate is almost fully consumed (~93% conversion). The starting amplitude is small and in the region of 0.05 pH units, but developed into 0.8-0.9 pH units with a period ranging from 10 to 40 min.

Chi-IM-PdCl$_2$ is subsequently fabricated into a macrogel (FIG. 2A), using additional chitosan solution and genipin as a cross-linker and incorporating fluorescein as a model drug compound. Upon drying, these crosslinked macrogels (denoted as Chi-IM-PdCl$_2$ macrogels) form a thin layer membrane (~1 mm thickness). The final gel consists of a chitosan matrix with swollen (crosslinked) Chi-IM-PdCl$_2$ particles statistically distributed in it.

Figure 2:
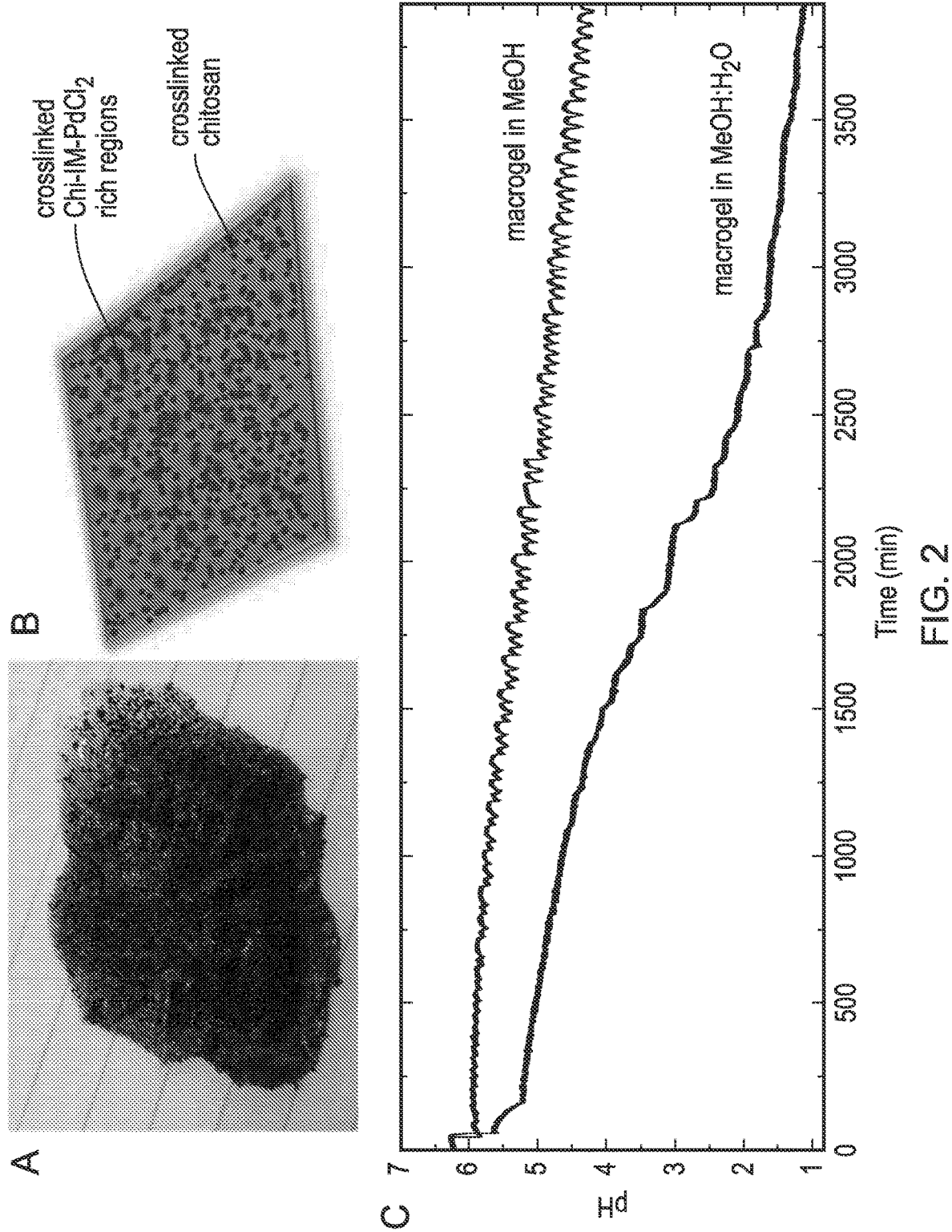
FIG. 2 shows A) Chi-IM-$PdCl_2$ macrogel top view. B) Scheme of distribution of chitosan and Chi-IM-$PdCl_2$-rich regions in the fully cross-linked gel. C) pH trends recorded in the PCOC system employing Chi-IM-$PdCl_2$ macrogels as a catalyst and PhAc as a reactant in methanol (black line, top) and methanol:water (grey line, bottom).

Changes in pH in the PCOC reaction system are studied in two different solvent systems—pure methanol and a methanol:water system (1:1). The reaction is initiated by addition of hydroiodic acid. As can be seen in FIG. 2B, recurrent non-linear trends in the time series are observed in both solvent systems, however, they have different patterns and significantly different pH ranges.

In methanol, the macrogel gives regular pH oscillations, starting almost immediately after addition of HI (therefore at higher pH values) and sustained over the whole course of the reaction, with a period ranging from 30 to 60 min and amplitude of 0.1-0.2 pH units. While pH in methanol does not correlate directly with hydrogen ion concentration, higher pH values still indicate smaller hydrogen ion concentrations and in this case small hydrogen ion amplitudes. This result indicates the prevalence of autocatalytic steps at higher pH values. No Pd leakage is detected in the system at the beginning and at the end of the runs. After removal of the gel, no further starting material conversion is observed.

In contrast to the pH behaviour observed in neat methanol, pH decreases stepwise without recovering in methanol:water solvent mixture, indicating that the reaction responsible for the pH recovery is either inhibited or concealed by the presence of water.

Figure 3:
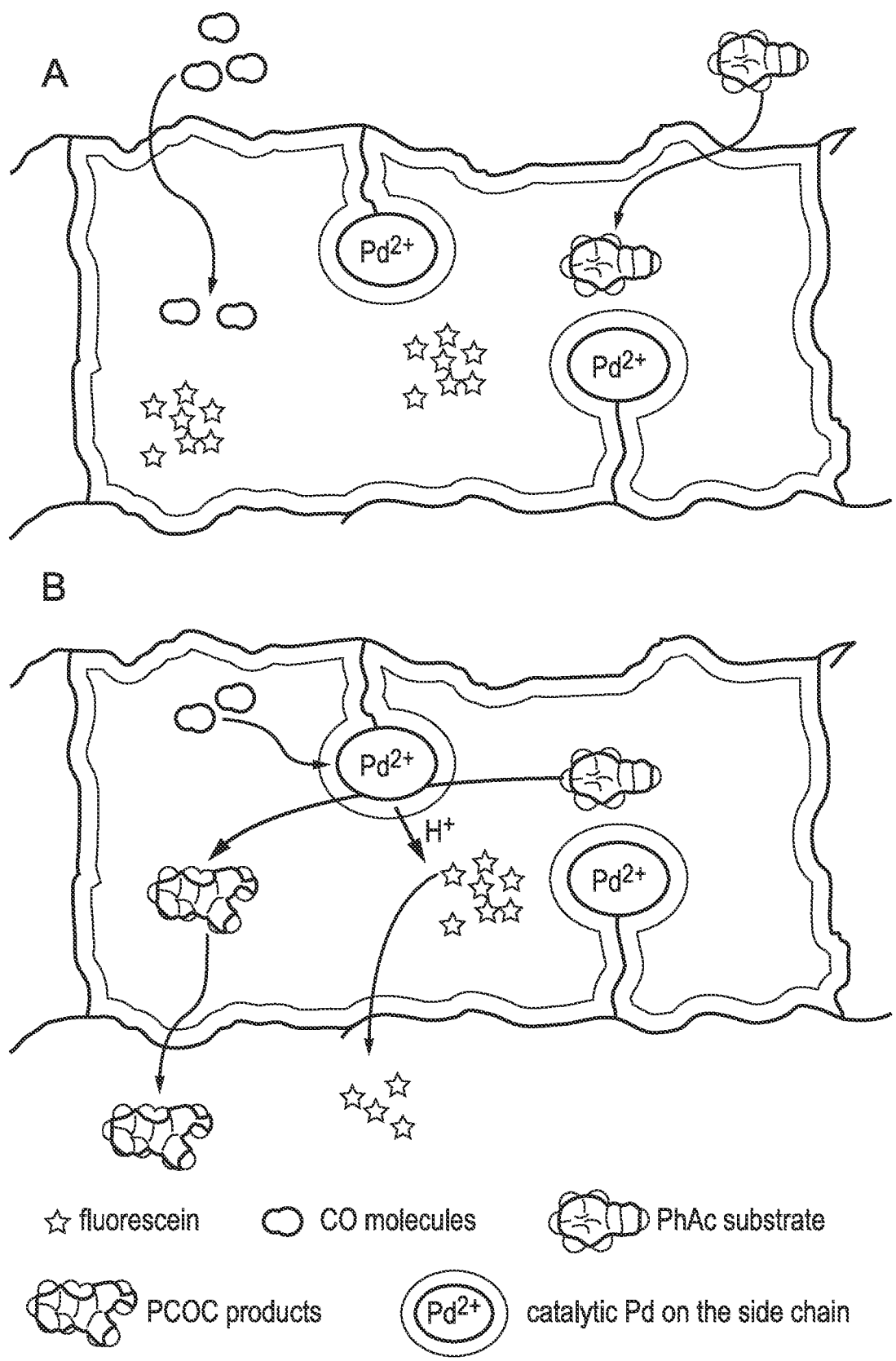
FIG. 3 shows A) Diffusion stage of the PCOC reaction in the macrogels. B) Conversion and release stage of the PCOC reaction in the macrogel. C and D) pH-associated pulsed conversion indicated by the concentration of starting material (PhAc) as a function of time in methanol (C) and methanol:water (D). pH-associated pulsed release of Z-isomer as a function of time in methanol (E) and in methanol:water (F) system. PhAc and Z-isomer concentrations are shown with closed symbols, the connecting lines are only as a guide for the eye and do not represent actual data. The start of each pulse release in methanol is indicated by a dotted vertical line.
Figure 3:
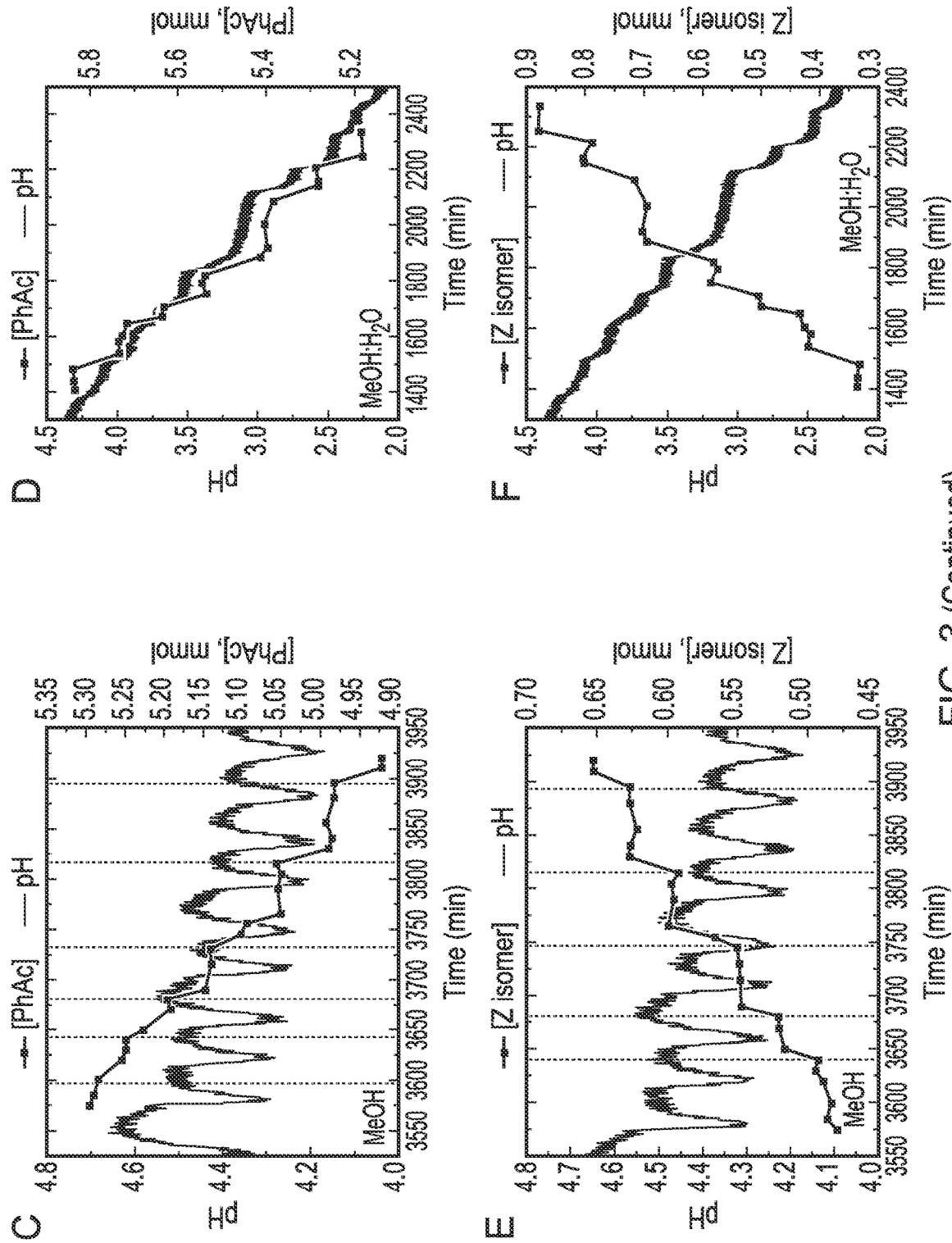

Since the catalytic system in this work is heterogeneous and incorporated within the macrogel, diffusion of the substrate to the gel surface and/or into the gel is needed for reaction to take place (FIG. 3A). Similarly, the release of reaction products occurs in the opposite direction (FIG. 3B). In both solvent systems, the macrogel exhibits a pulsed release of products, independent of whether the pH oscillates or decreases stepwise. The transfer of products back to the bulk reaction system is not diffusion driven, i.e. it does not go in the direction of concentration decrease.

FIGS. 3C and 3D show the evolution of starting material conversion, while the FIGS. 3E and 3F show release of product dimethyl (2Z)-2-phenyl-2-butenedioate (denoted as Z-isomer).

Figure 4:
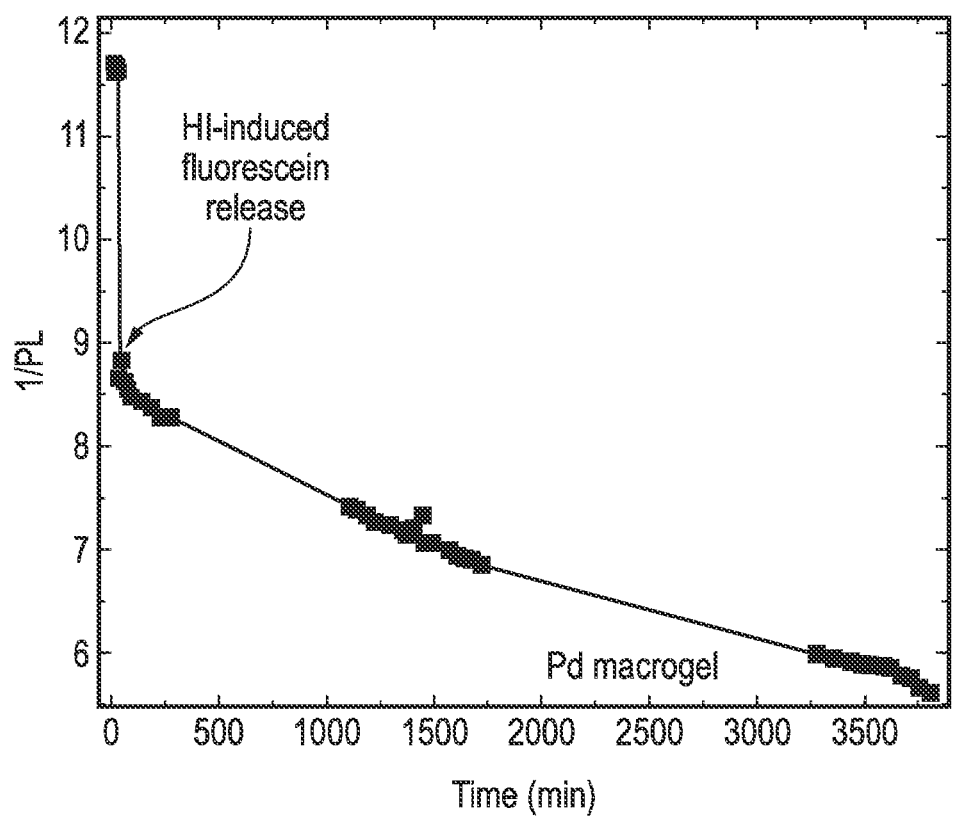
FIG. 4 shows the release of fluorescein from Chi-IM-$PdCl_2$ macrogel in methanol, expressed as inverse photoluminescence intensity (1/PL). The connecting lines are only as a guide for the eye and do not represent data.

In methanol, product formation correlates to pH fall within a single oscillation, while in methanol:water, product formation fully correlates to the pH drop within a single step.

pH-controlled release of an agent is studied using fluorescein sodium salt as a photoluminescence tracer incorporated within the macrogel during the fabrication process, with the intensity of photoluminescence (PL) of the reaction solution measured at 530 nm (excitation 480 nm). The macrogels do not demonstrate any fluorescein release until the addition of HI, which causes a significant increase in emission intensity in Pd-containing macrogel solutions. FIG. 4 shows evolution of PL intensity versus time, represented as 1/PL. As the oscillations proceed, the PL intensity keeps rising until the end of the reaction.

Figure 5:
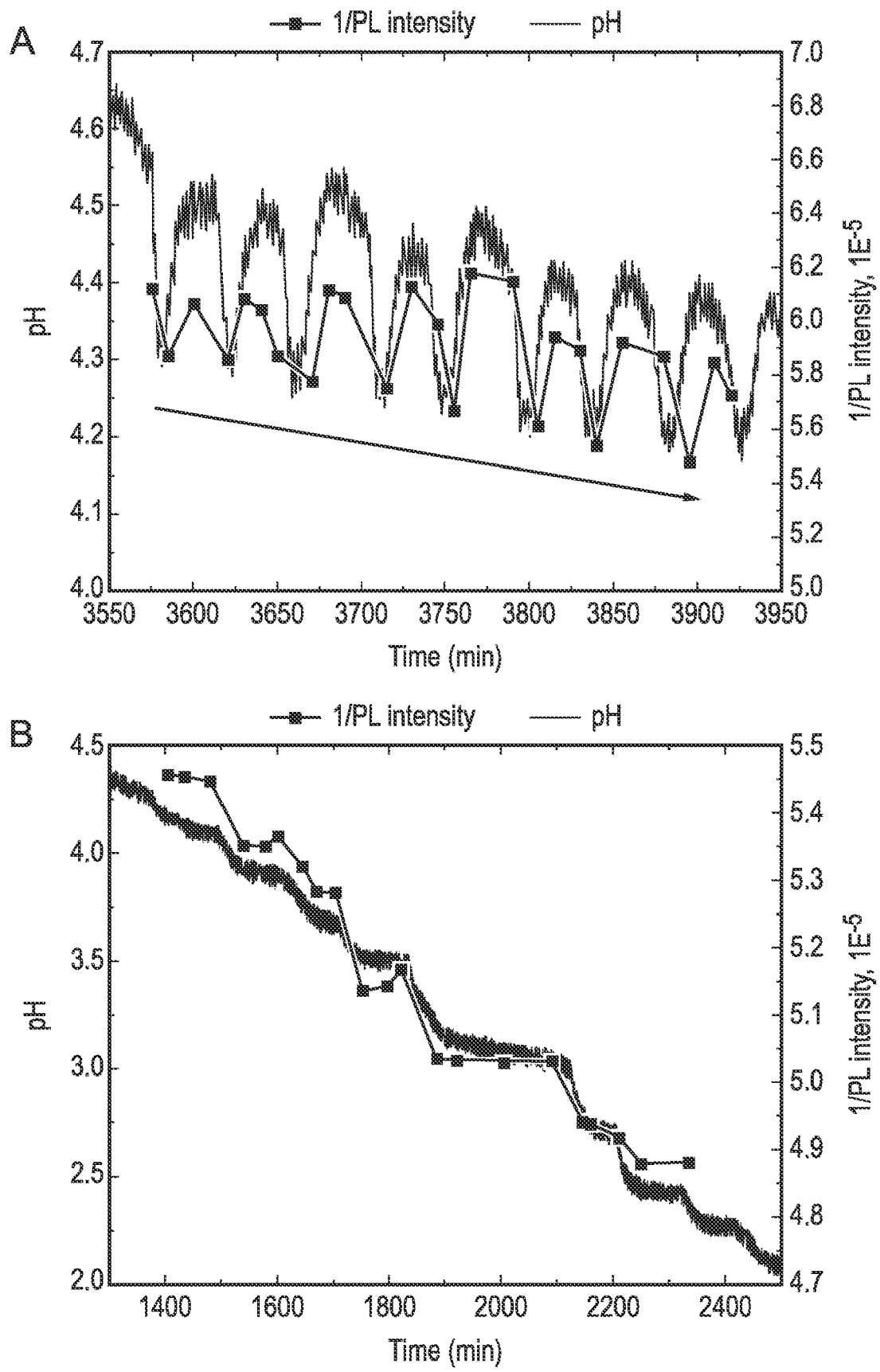
FIG. 5 shows that the pH-controlled release of fluorescein as a function of time in (A) methanol and (B) in methanol:water systems. Inverse PL intensity is presented as closed symbols. The connecting lines are only as a guide for the eye and do not represent data.

A closer look at the character of fluorescein release in methanol (FIG. 5) reveals that release of fluorescein occurs in oscillatory mode, fully synchronised with oscillations in pH. The maximum PL intensity is observed when pH is low and when the pH increases, the PL from fluorescein decreases. This suggests that fluorescein is released and then reabsorbed by the macrogel, which further suggests that certain changes occur in the gel in response to pH oscillations, even though the gel has collapsed in methanol. While reaction rate governs substrate conversion to products in a stepwise manner, fluorescein release appears diffusion-governed. The gradual decrease in 1/PL is correlated with a gradual decrease in pH which again indicates a link to changes in macrogel volume and porosity. The general dependency of fluorescein PL on pH also should not be fully excluded, however, reports have shown that PL intensity increases directly according to pH increase. Here, we observed an opposite process.

The same macrogel in methanol:water demonstrates a totally different behaviour (FIG. 5B). Fluorescein is not reabsorbed but released in steps which correlate with a decrease in pH. This again suggests diffusion controlled fluorescein release, aligned with a stepwise decrease in pH and an anticipated stepwise increase in macrogel volume. A decrease in pH, i.e. increase in hydrogen ion concentration, is believed to induce swelling in chitosan based hydrogels due to the protonation of —NH$_2$ groups resulting in an increase in porosity and therefore increase in load diffusion.

To conclude, using chitosan-based palladium catalyst macrogels, we employed an oscillatory oxidative carbonylation reaction as a driving force to establish a pulsed release of 'drug-like' fluorescein in both neat methanol as well as methanol:water (1:1) systems. In methanol, fluorescein is released in an oscillatory manner, while in the methanol:water system, release is stepwise. These results fully correlate with pH trends recorded in these systems, indicating diffusion driven release aligned with anticipated changes in macrogel volume as a function of pH. In both solvent systems we confirmed the stepwise conversion of reactant as well as stepwise formation of the reaction products suggesting that the rate of reaction determines this process.

1. Materials

Materials are used as received: palladium chloride (>99.9%), chitosan medium molecular weight, 2-pyridinecarboxaldehyde (99%), sodium chloride (ACS reagent, >99.0%), genipin (>98% (HPLC), hydroiodic acid (57%), phenylacetylene (98%), methanol (HPLC Plus, >99.9), all Sigma Aldrich); naphthalene (extra pure), potassium iodide (>99% GPR RECTAPUR®), all VWR Chemicals; buffer solutions: pH 2.00 (glycine), pH 7 (phosphate) and pH 10 (borate) (all NIST Standard, ready to use for pH measurement, Fisher Chemical). Pure air and carbon monoxide are supplied by BOC.

2. Synthesis and Characterisation of Chi-IM-PdCl$_2$

Chitosan (0.500 g) is mixed with 0.300 g of 2-pyridinecarboxaldehyde in 50 mL of diethyl ether over water-absorbing particles (40 mesh) for 18 h. Precipitate is separated from particles, collected by filtration and dried in vacuo overnight to yield 0.522 g of Chi-IM polymer.

Resulting Chi-IM polymer (0.522 g) is stirred with 250 mg of Na$_2$PdCl$_4$ in 50 ml of methanol to yield (0.703 g) of Chi-IM-PdCl$_2$. Pd content is measured by inductively coupled plasma optical emission spectrometry (ICP-OES) as 14.27%.

3. Gas Chromatography with Mass Spectrometry Detector (GC-MS)

The samples are analysed for starting material conversion and product distribution by a Varian Saturn 2200 Gas chromatography with Mass spectrometry detector (GCMS) fitted with a VF-5 ms column (30 m). The method is as follows: injector temperature 150° C.; helium flow rate 1 mL min-; oven temperature 100-195° C. over 35 min in 5 steps. All samples are taken at their indicated time intervals of the experimental runs (unless otherwise stated within the main text) and filtered over silica prior to being diluted 1:2 with methanol.

4. Photoluminescence (PL)

PL intensity is measured by FLUOstar® Omega UV-Vis filter-based multi-mode microplate reader, using 480 nm filter for absorbance and 530 nm filter for fluorescence collection. For measurements, 0.2 mL of sample solution are deposited per well and three scans taken.

5. PCOC Using Chi-IM-PdCl$_2$ as a Catalyst

Reaction is performed at approximately 20° C. in a flat-bottom Erlenmeyer flask (100 mL) at constant stirring, using HEL micronote system to log pH and temperature within the bulk of the reaction. Prior the reaction, pH probe is calibrated at room temperature against NIST-traceable buffer solutions of pH 2, 7 and 10. 4.150 g of KI, 200 mg of Chi-IM-PdCl$_2$ catalyst and 256 mg of naphthalene (internal standard) are charged into the flask in their solid state and suspended in 100 mL HPLC grade methanol by stirring. The pH and temperature monitoring starts while the solids are dissolving and continue throughout the experiment. Stabilisation of pH indicates that the dissolution of KI is complete. Then, the CO and air purging through the solution at flow rate of 15 mL/min each commences. After initial pH drop, it stabilises, and 1.38 mL (12.57 mmol) of phenylacetylene is added. The pH and temperature are monitored for 2000 min. The samples of the reaction mixture are taken at the end of the reaction and analysed using GC-MS method described above to determine starting material conversion as well as product content. Products are observed in significant amounts: dimethyl (2E)-2-phenyl-2-butenedioate (E-isomer)=6.7 mmol; 5,5-dimethoxy-3-phenyl-2(5H)-furanone (DMO)=5.4 mmol; dimethyl (2Z)-2-phenyl-2-butenedioate (Z-isomer)=0.2 mmol. Beside the main products, some other products are observed, too, which are generally perceived as intermediates: 4-methyl-atropate=0.14 mmol; phenyl cinnamate=0.025 mmol.

6. Macrogel Fabrication

Chi-IM-PdCl$_2$ containing gels are fabricated as follows: 2 mL of chitosan solution 1% in 1% acetic acid, 0.100 g of Chi-IM-PdCl$_2$ catalyst, 0.200 mL of genipin 1% solution in water and 0.2 mL of 5% wt fluorescein solution in 1% aqueous sodium hydroxide are all charged onto a plastic diamond-shaped weighing boat (dimensions 80 mm×50 mm×14 mm), evenly distributed on the bottom and thoroughly mixed together. The weighing boat is closed with a heavy plastic lid, heated in air for 24 h to give a flat hydrogel of emerald colour with inserts of dense particles of the catalyst.

7. Macrogel PCOC Procedure in Methanol Only 4.150 g of KI and 0.128 g of naphthalene is dissolved in methanol (50 mL) in a 100 mL beaker. The macrogel is inserted into the solution and a small stir bar (5 mm) added on the side. The pH and temperature probes are kept away from touching the gel. The pH is left to stabilise and then CO/air is purged through the solution at 15 mL/min each. After 15 min of purging, 0.69 mL (6.28 mmol) of phenylacetylene is added to the reaction. After the pH stabilises again, 0.1 mL of dilute HI solution is added (0.0228 mmol) to induce oscillations. The reaction is monitored for 4000 min. Samples (0.4 mL) for product release and PL intensity measurements are withdrawn at indicated time points.

8. Macrogel PCOC Procedure in Methanol:Water System 0.064 mg of naphthalene is dissolved in 25 mL of methanol, then 25 mL of DI water is added under continuous mixing. Resulting solution is used to dissolve 4.150 g of KI in a 100 mL beaker. The macrogel is inserted into the solution and a small stir bar (5 mm) is added on the side. pH is left to stabilise and then CO/air is purged through the solution at 15 mL/min each. After 15 min of purging, 0.69 mL of phenylacetylene is added to the reaction. After the pH stabilises again, 0.1 mL of dilute HI solution is added (0.0228 mmol) to shorten the induction time. The reaction is monitored for 4000 min. Samples (0.4 mL) for product release and PL intensity measurements are withdrawn at indicated time points.

Example 2—poly(2-(1-(4-vinylbenzyl)-1H-1,2,3-triazol-4-yl)pyridine) (polyVBTP)

Polymer-supported palladium (PS-VBTP-PdCl$_2$) catalyst is synthesised from commercially available Merrifield resin in three simple steps with a near quantitative conversion according to the following scheme.

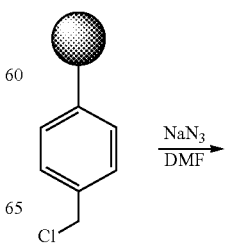

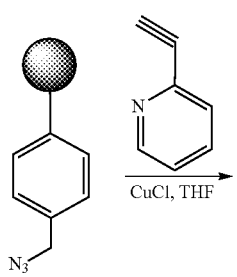
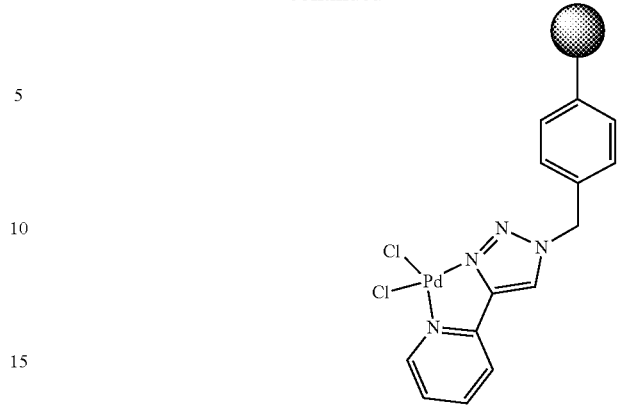

At first, the resin is converted into the azide-derivative which is then reacted with 2-ethynyl pyridine via 'click' chemistry. Resulting triazole-pyridine resin is stirred with palladium (II) salt to yield palladium catalyst. The success of the click reaction is confirmed by Fourier Transform Infrared Spectroscopy (FTIR) which shows the absence of the azide band at 2100 cm$^{-1}$ after the 'click' reaction and increase in intensity of the bands associated with —N═ and —C—N— vibrations (1600 cm$^{-1}$ and 1415 cm$^{-1}$).

Figure 6:
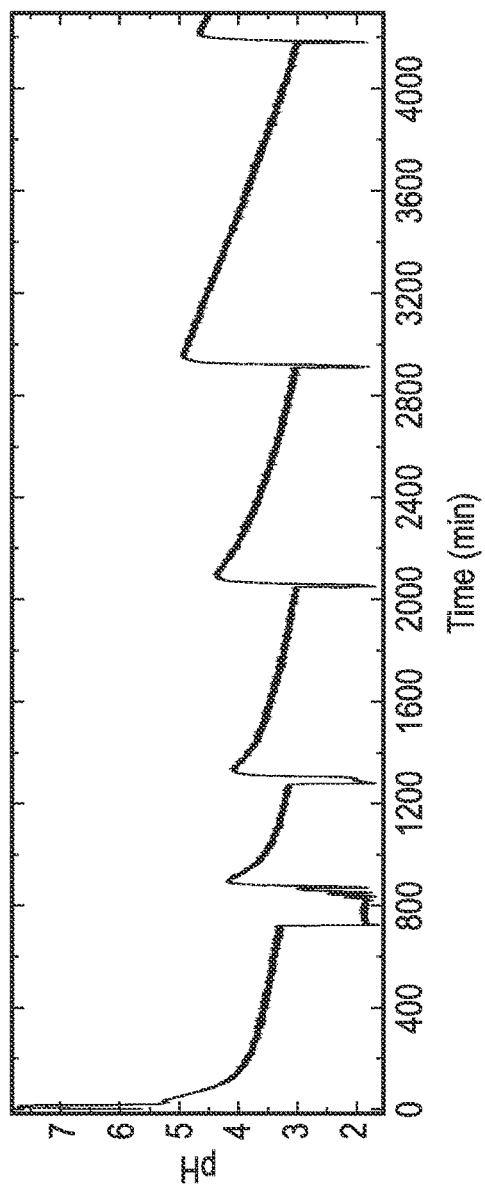
FIG. 6 shows pH oscillations in a catalytic system using PS-VBTP-$PdCl_2$.

The oscillatory behaviour of this catalyst in typical phenylacetylene oxidative carbonylation reaction is studied. FIG. 6 shows the produced pH pattern. Initially, there is a pronounced pH drop (from 7.7 to 5.3) when CO and air are purged through the reaction system and slow pH decrease when PhAc is added (to pH 3.3). However, after a 780 min of induction period another sharp pH drop is observed and the oscillations start shortly after that. The first three oscillations are relatively small with an amplitude of 0.5-1.2 and a period of 12-20 min, but then they change shape and grow in amplitude (2.4-3.3 pH units) and period (400-1260 min). The shape of the oscillations is trapezoidal, with only 35 min (on average) period between the maximum pH values of the previous and following oscillations.

Gel, incorporating VBTP, is synthesised according to the following scheme:

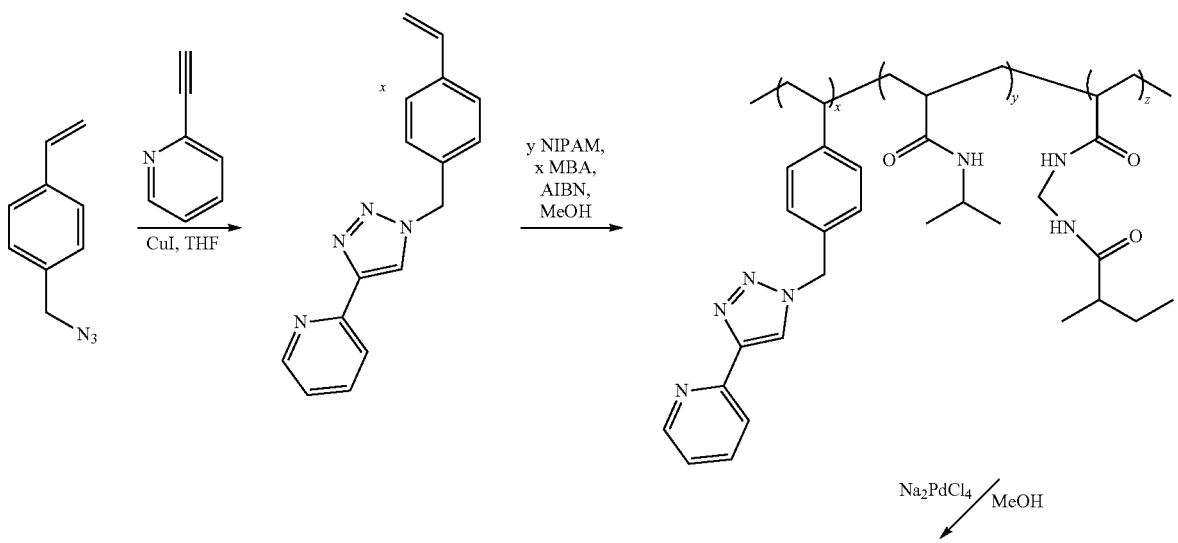

-continued

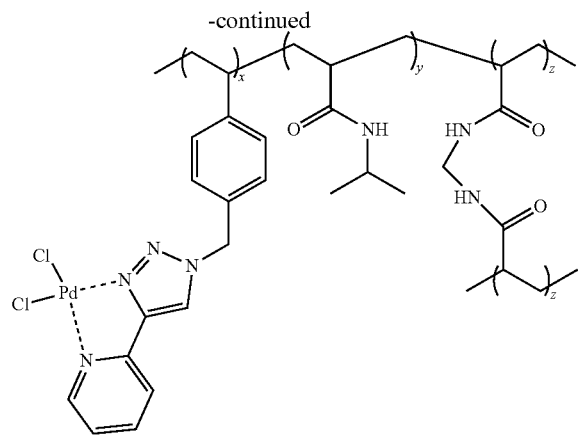

Figure 7:
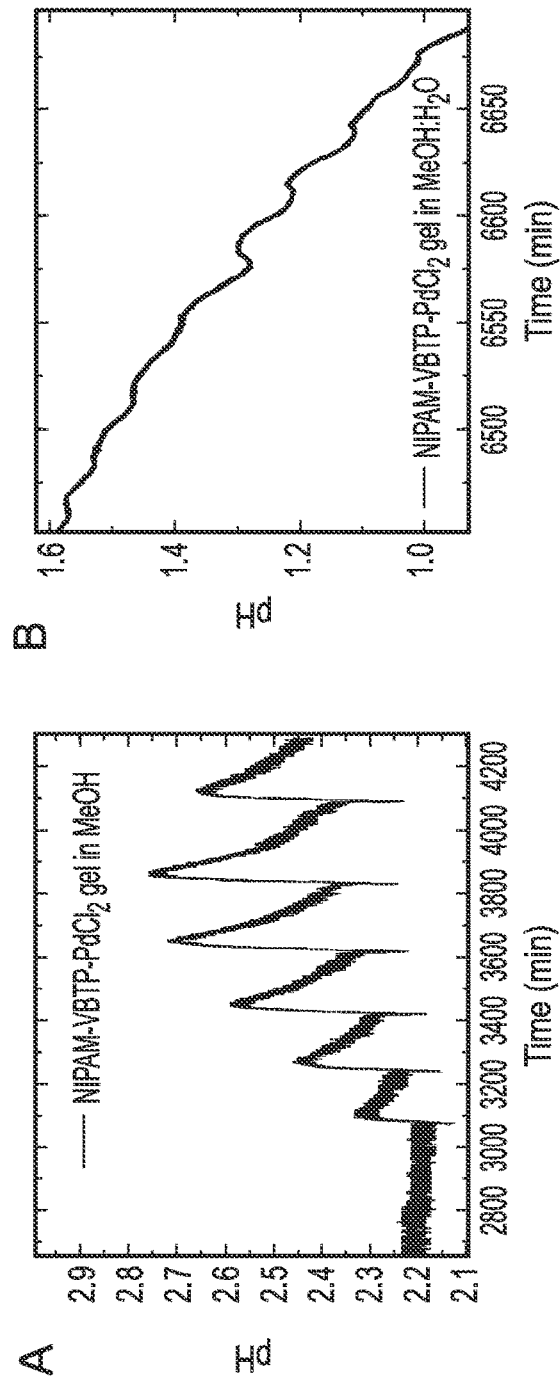
FIG. 7 shows pH oscillations in a NIPAM-VBTP-$PdCl_2$ gel in methanol only (left), in a NIPAM-$PdCl_2$ gel (right, black line) and NIPAM-VBTP-$PdCl_2$ gel in water:methanol mixture.

NIPAM-VBTP-PdCl$_2$ gel demonstrates oscillations in methanol (FIG. 7A), very similar in pattern to those generated by crosslinked PS-VBTP-PdC$_{l2}$ catalyst, with the only difference in length of induction period. In NIPAM-VBTP-PdCl$_2$ gel in methanol, oscillations start only after 3150 min and have a gradually increasing period (from 160 to 260 min) and amplitude (from 0.21 to 0.53 pH units). From the shape of the oscillations, it can be concluded that two processes of different rates govern the pH drop—one slow process, occurring straight after the pH reaches the highest point in the oscillations, and a fast process. For example, a slow process takes 182 min and the fast process only 3 min. At the same time, the pH rise occurs unusually fast, within 23 min on average, thus taking only 10-12.5% of one oscillation period. In other reported systems the pH rise whether is the longest process or takes about 50% from the whole oscillation period.

In water:methanol mixture (FIG. 7B), NIPAM-VBTP-PdCl$_2$ gel demonstrated a general trend for pH decrease from 2 to −0.4 pH units which only occur in 6000 min after substrate addition. The pH decrease has a wave-like pattern, reminiscent of a stepwise decrease in chitosan systems in water:methanol, however, in case of NIPAM-VBTP-PdCl$_2$ gel the pH seems to recover slightly after a step of decrease. The 'waves' have 30-40 min period and only recover 0.03-0.05 pH units.

1. Synthesis of Crosslinked Poly(Styrene-r-Vinylbenzyltriazolepyridine) Impregnated with PdCl$_2$ (PS-VBTP-PdCl$_2$)

Merrifield resin (1.500 g) is stirred with 3.000 g of NaN$_3$ in 20 mL of DMF at room temperature for 48 h. When complete, reaction mixture is filtered and the solids are collected on the filter and washed with water (3×200 mL) and acetone (100 mL). Resulting powder is dried in vacuo to give 1.610 g of poly(styrene-r-vinylbenzylazide) (PS-VBA).

0.500 g of resulting resin PS-VBA and 0.020 g of dry copper chloride (1) is suspended in 20 mL of anhydrous THF. Reaction mixture is purged with nitrogen for 20 mL, after which 0.2 mL of ethynyl pyridine is added via a syringe. Reaction is stirred for 24 h at ambient temperature under inert atmosphere. When complete, the reaction mixture is filtered and the solids collected on the filter and washed with THF and water multiple times (until the filtrates ran clear). Resulting solids are dried in vacuo to yield 0.900 g of yellowish product (PS-VBTP).

0.700 g of PS-VBTP is stirred with 50 mg of Na$_2$PdCl$_4$ for 24 h in methanol under nitrogen atmosphere. The resin is then filtered, washed with methanol and dried in vacuo to give 0.742 mg of pale yellow powder (PS-VBTP-PdCl$_2$).

2. Synthesis of 2-(1-(4-vinylbenzyl)-1H-1,2,3-triazol-4-yl)pyridine (VBTP)

Vinyl benzyl azide (0.500 g) and CuCl (1) (0.010 g) are mixed in 20 mL of dry THF for 15 min and purged with nitrogen for 20 min before 0.196 mg of ethynyl pyridine is added slowly via syringe to the solution. Reaction is stirred at ambient temperature for 24 h, then THF is evaporated. The residue is extracted with diethyl ether (100 mL) and washed with water (2×200 mL), organic phases collected and solvent evaporated. The resulting dry residue is recrystallized from hot hexane (100 mL) with a drop of methanol (to assist dissolution), filtered and collected. The white crystals are dried in vacuo (yield 97%, VBTP). $^1$H NMR (500 MHz, CDCl$_3$, δ ppm): 5.31 (d, 1H), 5.54 (s, 2H), 5.76 (d, 1H), 6.70 (dd, 1H), 7.20 (t, 1H), 7.28 (d, 2H), 7.40 (d, 2H), 7.78 (t, 1H), 8.03 (s, 1H), 8.18 (d, 1H), 8.55 (d, 1H).

3. Synthetic Gel Fabrication (NIPAM-r-VBTP-r-MBA Gel)

0.480 g of N-isopropylacrylamide (NIPAM), 0.020 g of azobisisobutyronitrile (AIBN), 0.020 g of N,N'-methylenebis(acrylamide) (MBA) and 0.100 g of VBTP are loaded into a 22 mL glass vial, sealed with a turnover rubber stopper and equipped with a 5 mm magnetic bar. The vial contents are evacuated and backfilled with nitrogen three times before 2 mL of nitrogen-purged methanol is added. The reaction is stirred for 5 min before placing into a 65° C. heated oil bath. Polymerisation proceeds for 18 h after which the gel is taken out of the vial and washed with methanol multiple times to remove any unreacted material. Resulting gel is soaked in methanolic solution of Na$_2$PdCl$_4$ (1 mg/mL) for 48 h and then washed with methanol to remove any reactants that are not bound to the gel support.

4. PCPOC

Reaction is performed in a flat-bottom beaker (50 mL) at constant local stirring (small 5 mm magnetic bar), using HEL Micronote system to record pH and temperature within the bulk of the reaction. Prior the reaction, probes are calibrated at room temperature (17-20° C.) against buffer solutions of 2, 7 and 10 pH. Stated amounts of KI (2.075 g) and catalyst (whole gel or 200 mg of resin) are charged into the flask in their solid state and dissolved in 50 mL HPLC grade methanol or water:methanol (50:50 v/v % system). The pH monitoring is initiated while the solids are dissolving with the stabilisation of pH taken as indication of the completed dissolution of KI. At that point, purging through the solution with the CO (15 mL/min) and air (15 mL/min) commenced. After 10-20 min (or after stabilisation of pH following initial drop), phenylacetylene (1.38 mL) is added. In 10 min, 0.028 mmol HI is added. The system is monitored onwards for changes in pH and temperature of the reaction.

All samples are taken in the end of the experimental runs (unless otherwise stated within the main text) and filtered over silica prior to being diluted 1:2 with methanol.

Example 3—Chitosan and Chitosan Proline Based Systems

Proline-functionalised chitosan is synthesised using a standard EDCI/DMAP coupling approach.

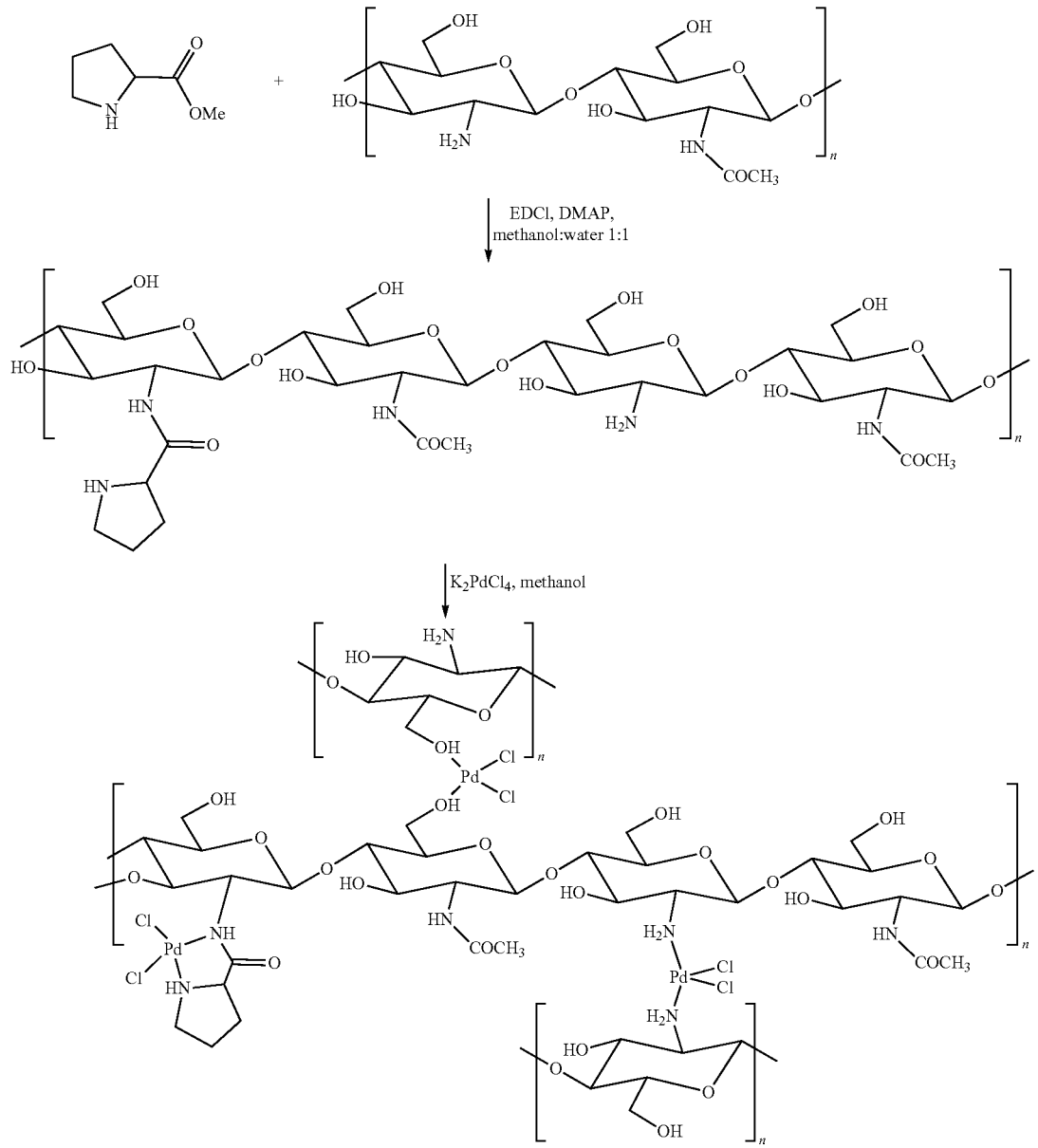

The samples are analysed for starting material conversion and product distribution by a Varian Saturn 2200 Gas chromatography with Mass spectrometry detector (GCMS) fitted with a VF-5 ms column (30 m). The method is as follows: injector temperature 150° C.; helium flow rate 1 mL min$^{-1}$; oven temperature 100-195° C. over 35 min in 5 steps.

The success of synthesis is confirmed by FTIR, where the relative change of intensity of the amide band at 1640 cm$^{-1}$ increases due to the formation of additional amide bonds and the intensity of the C—N amino band at 1380, 1300 and 1080 cm$^{-1}$ decreases. Subsequently, proline-functionalised chitosan is stirred with $K_2PdCl_4$ in methanol to yield Chi- Pro-Pd catalyst. It's important to note that chitosan has multiple binding ligands for Pd even prior to functionalisation, and since Pd requires bidentate binding, it may utilise the ligands on different chitosan chain, thus crosslinking them. After functionalisation, Chi-Pro-Pd becomes insoluble in 1% acetic acid (typical solvent). The content of Pd in Chi-Pro-Pd is 6.85 wt %.

Figure 8:
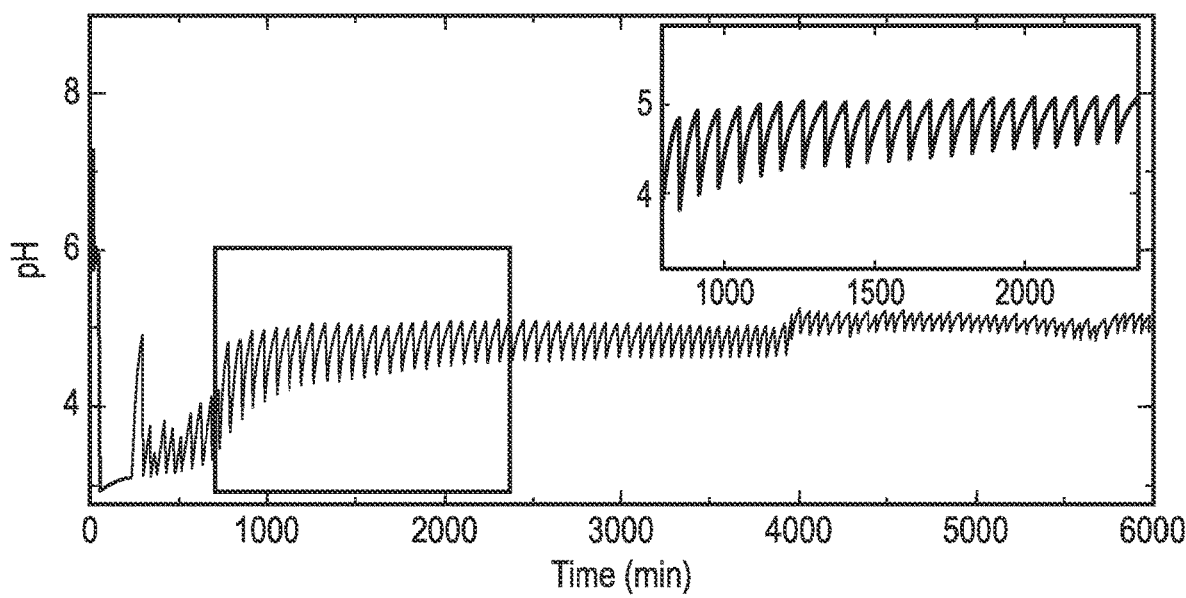
FIG. 8 shows pH trace of Chi-Pro-Pd catalysed carbonylation reaction using phenylacetylene as a substrate.

Chi-Pro-Pd catalyst is employed in the PCOC reaction with constant pH monitoring, first using phenylacetylene as substrate. The oscillations (FIG. 8) start in 190 min after addition of substrate, having a period of 49-69 min and an amplitude gradually varying between 0.2 and 1.82.

Figure 9:
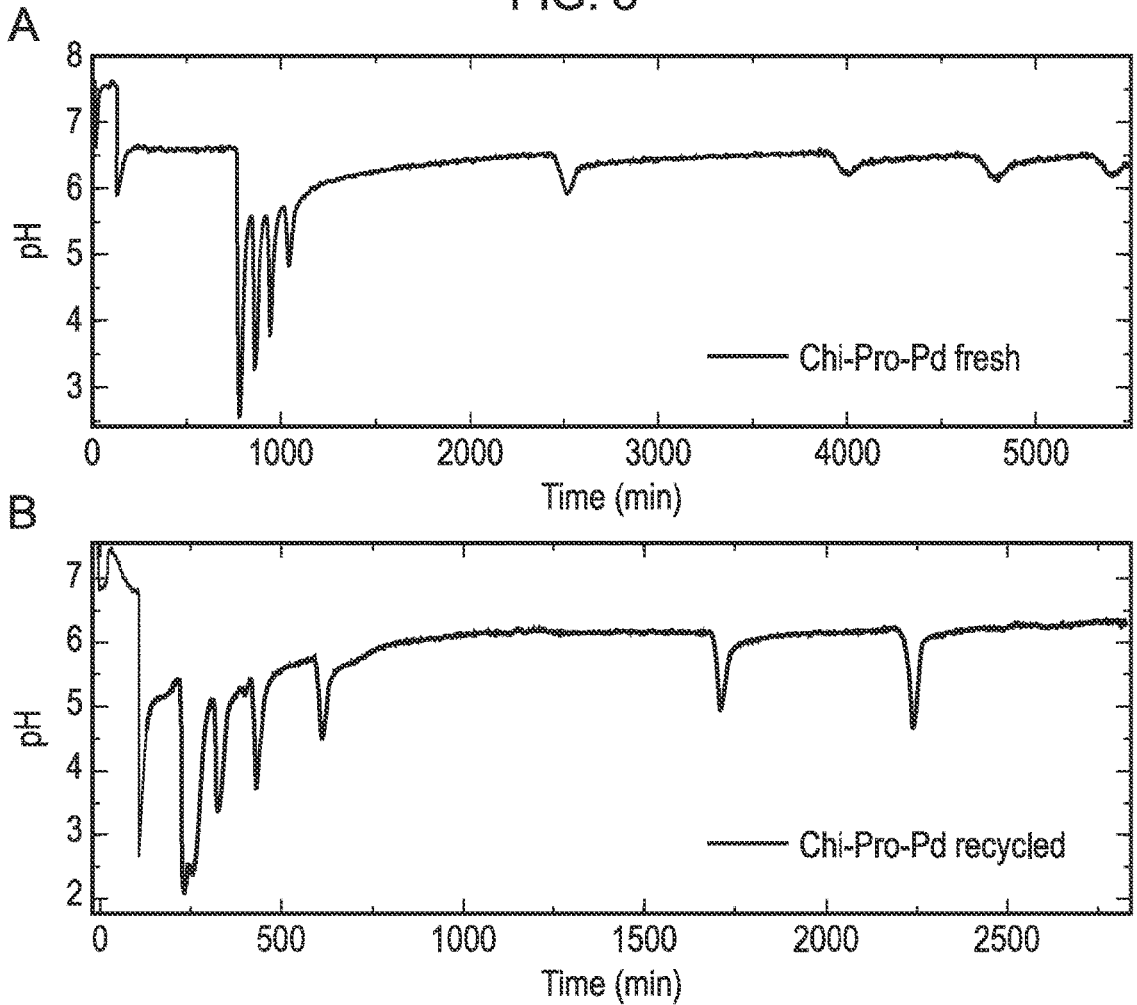
FIG. 9 shows pH trace of Chi-Pro-Pd catalysed carbonylation reaction using PEGDA as a substrate, in fresh catalyst (A) and recycled (B).

Chi-Pro-Pd catalyst is employed in the PCOC reaction, using polymeric dialkyne functionalised PEG polymer— polyethyleneglycolyl bis(pent-4ynoate) ester (PEGDA)—as a substrate. In Chi-Pro-Pd catalysed reaction (FIG. 9a), the addition of substrate does not lead to immediate pH drop, instead the pH increases marginally and after 10 min experiences a sudden drop from 7.5 to 5.8, from where it recovers to 6.45 pH units. At 750 min, a series of 'cascade' oscillations is observed, gradually decreasing in amplitude from 4.12 units to 1 and in period from 87 min to 66 min. After the first series of oscillation, the next pH drop only occurs at 2440 min. The second series of oscillations has much smaller amplitudes and much longer periods that tend to get shorter—from 1480 min to 604 min. If the same catalyst is recycled in the same conditions in a fresh reaction batch (FIG. 9b), the oscillation pattern is preserved (i.e. first a single pH drop and recovery, then a series of large oscillations, followed by smaller oscillations at increased periods), however, the time scales are much shorter. Thus, in recycled Chi-Pro-Pd, the first series of oscillations starts at 225 min and is over by 700 min, whereas in fresh catalyst these oscillations only starts at 750 min and continue for another 750 min. Additionally, the later oscillations are more pronounced and can reach the amplitudes of 1.25-1.60 pH units.

This demonstrates oscillatory regime of proline-functionalised chitosan-palladium catalyst (Chi-Pro-Pd) in a palladium-catalysed carbonylation reaction, employing both small molecule and polymeric substrates. Chi-Pro-Pd polymer is capable of generating oscillations even after recycling in a second run, indicating that proline ligands are strong enough to hold palladium.

Synthesis of proline-functionalised chitosan-palladium catalyst: 0.500 g of chitosan, 0.450 g of proline hydrochloride, 0.025 mg of DMAP and 1.200 g of EDCI are suspended in 30 ml of methanol. Then 30 ml of water (pH 4) is added while stirring. The reaction mixture is allowed to stir overnight, filtered, the solids washed with methanol, collected and dried in vacuo, resulting in dark brown chitosan particles (Chi-Pro, yield 86%). Chi-Pro-Pd is stirred with 1 mg/mL $K_2PdCl_4$ in methanol for 24 h, filtered and washed with methanol to remove any unreacted $K_2PdCl_4$. The solids are collected, dried in vacuo, resulting in dark black particles (yield 90%, Chi-Pro-Pd).

Example 4—Polyacrylate Palladium

Figure 10:
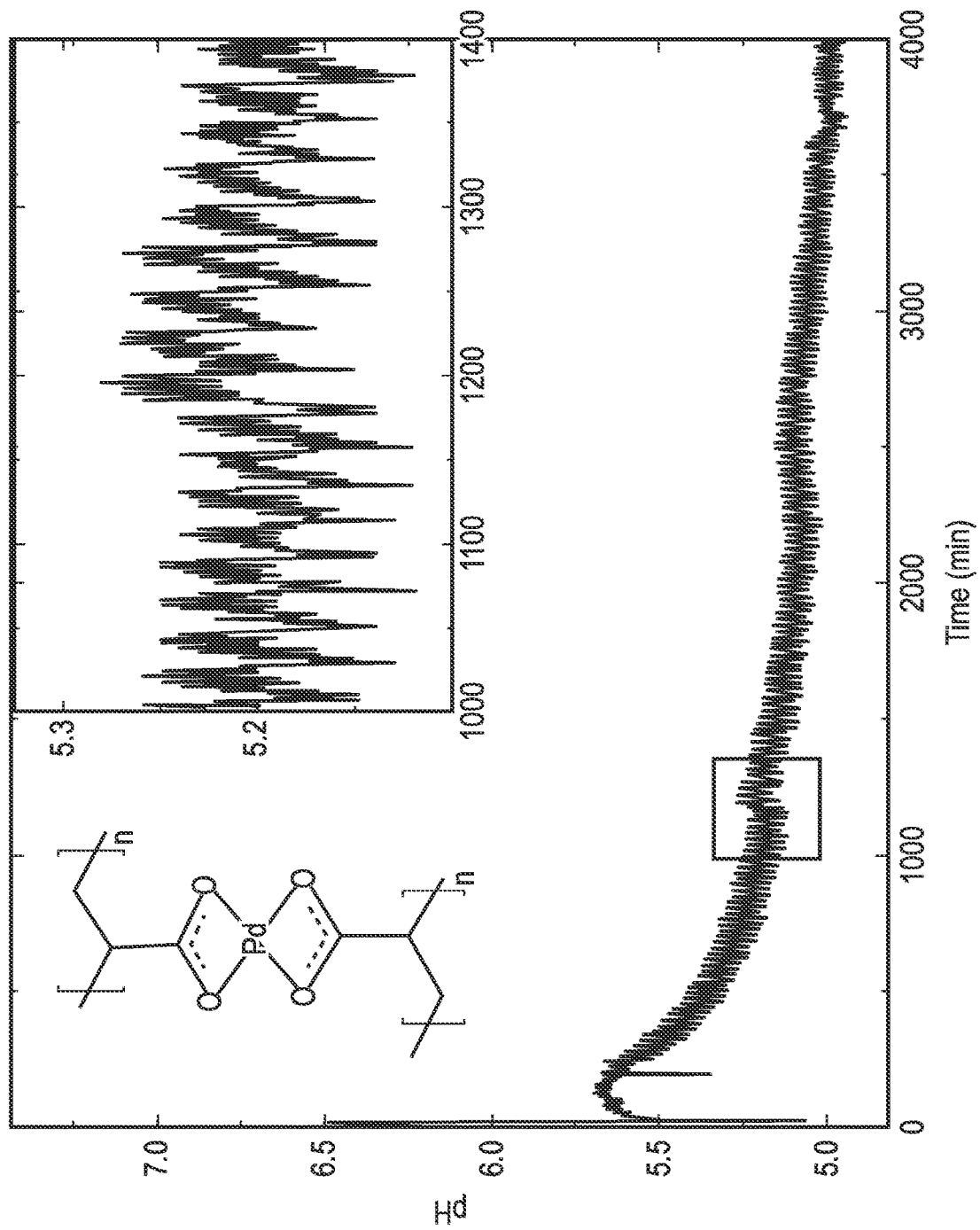
FIG. 10 shows pH recorded in PCOC of phenylacetylene (PhAc) in methanol using polyacrylate-Pd catalyst. The structure of the catalyst is shown as an inset.
Figure 11A:
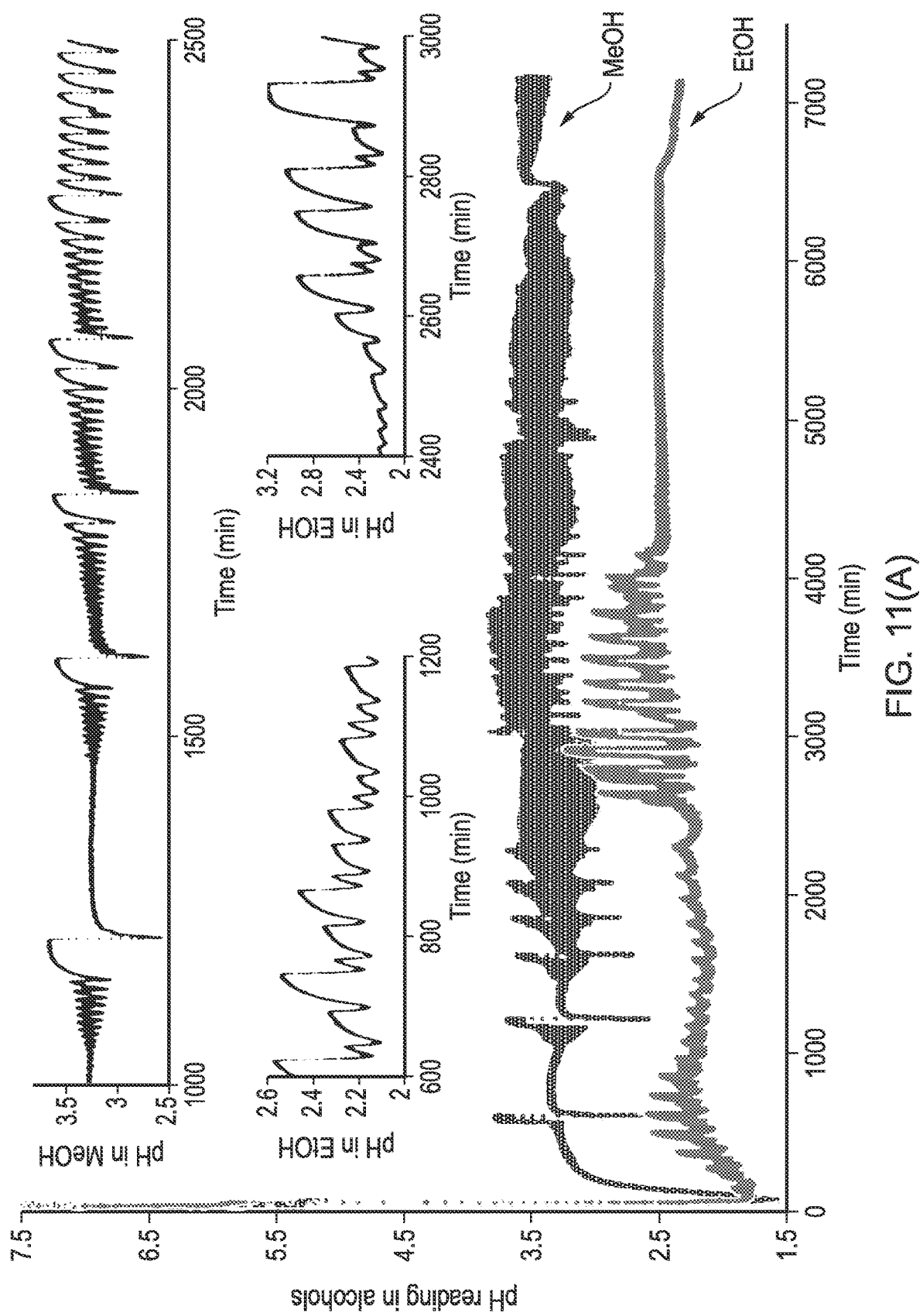
FIG. 11 shows A) pH recorded in the oxidative carbonylation reaction using PhAc/Pd-polyacrylate in MeOH (top line), and EtOH (bottom line), and B) pH recorded in the oxidative carbonylation reaction using PhAc/Pd-polyacrylate in 1-PrOH (top line), 1-BuOH (middle line) and 1-HexOH (bottom line).
Figure 11B:
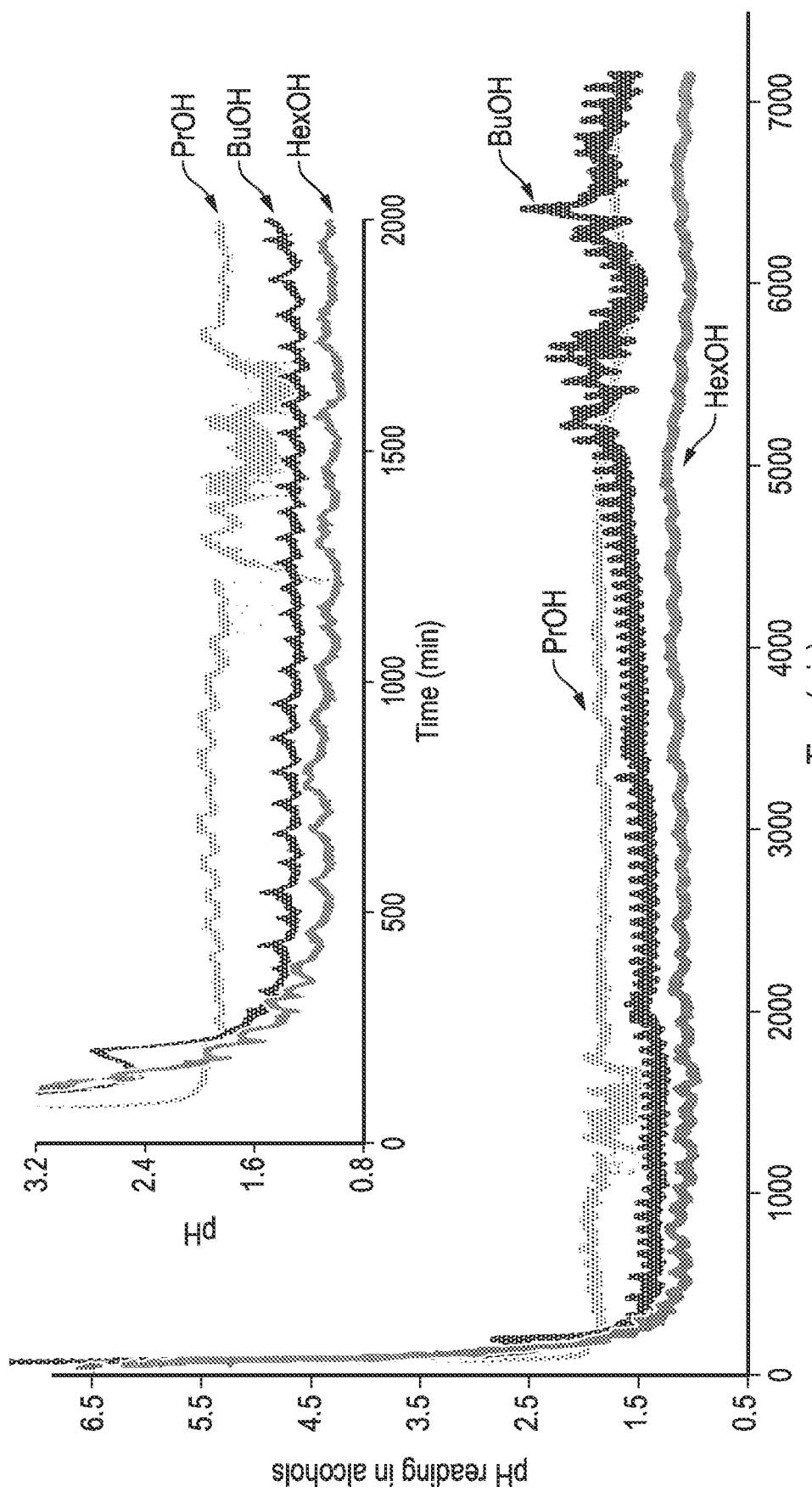
Figure 12:
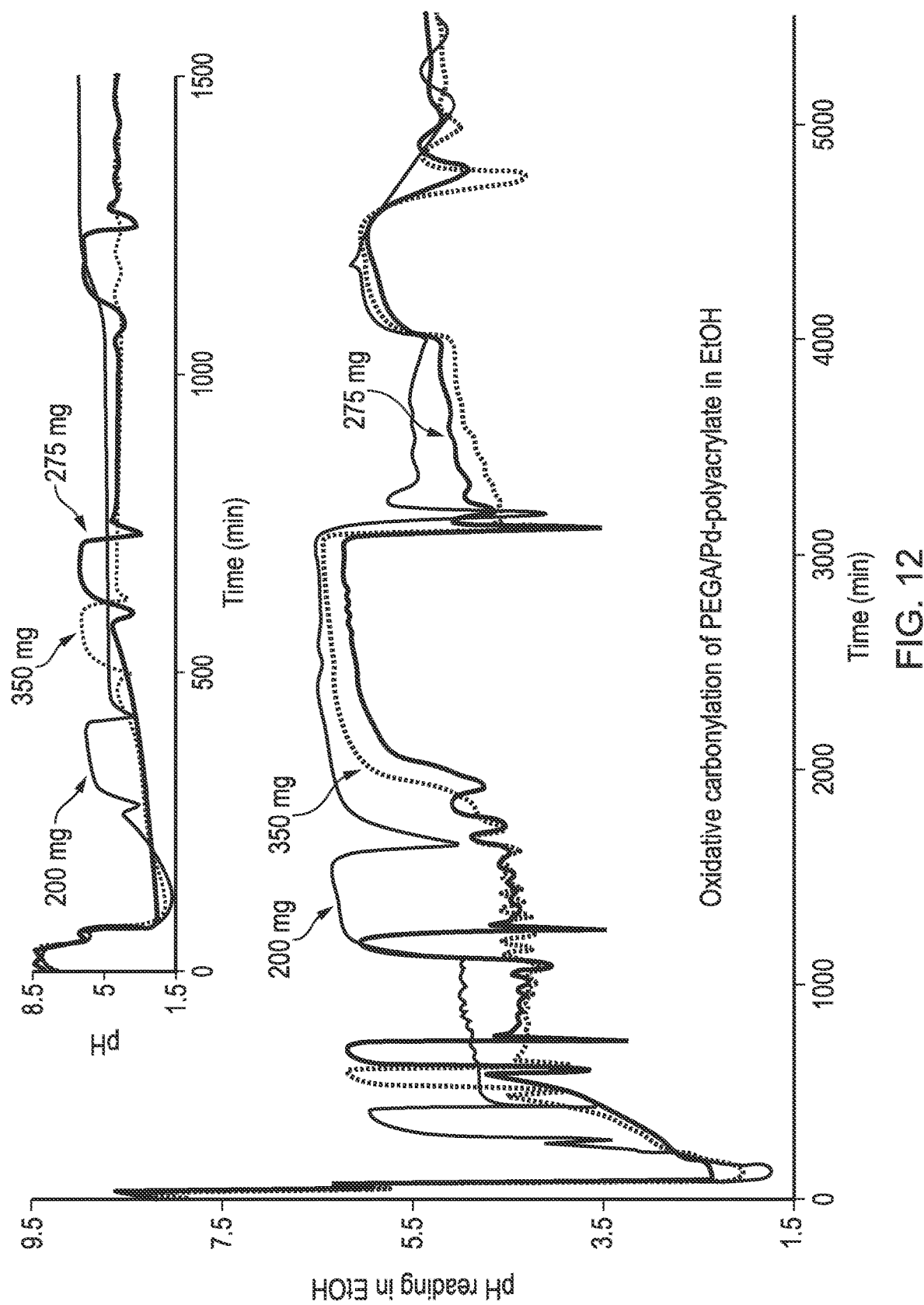
FIG. 12 shows pH recorded in the oxidative carbonylation reaction using PEGA/Pd-polyacrylate in EtOH using 200 mg, 275 mg and 350 mg of PEGA.
Figure 13:
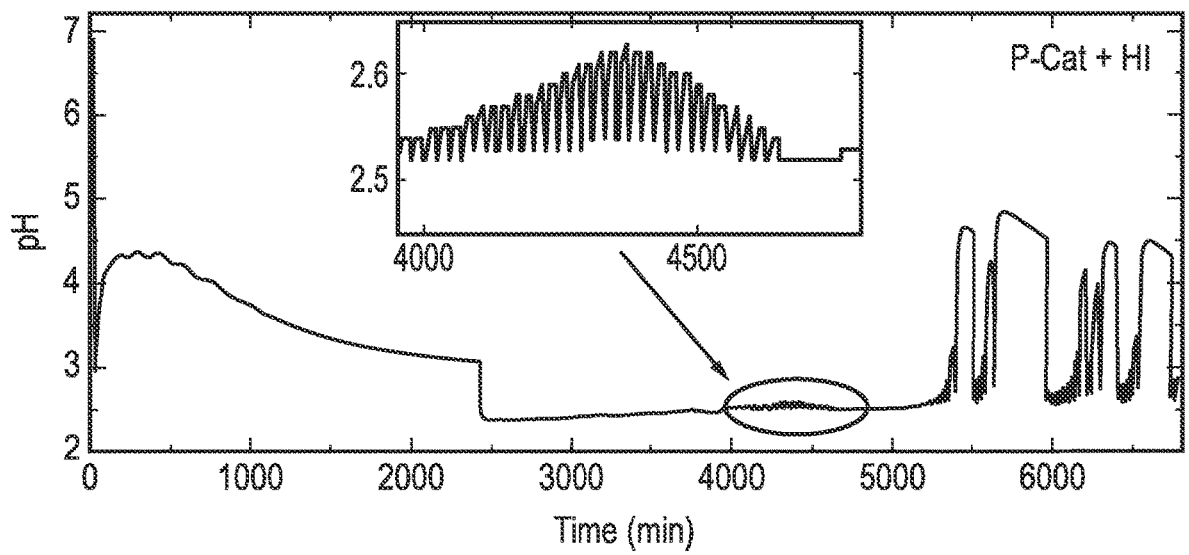
FIG. 13 shows pH recorded in the P-cat catalysed PCOC of phenylacetylene in methanol using CO/air (each 15 mL min$^{-1}$ at room temperature). Following the addition of PhAc substrate, 0.0228 mmol HI was added.
Figure 14:
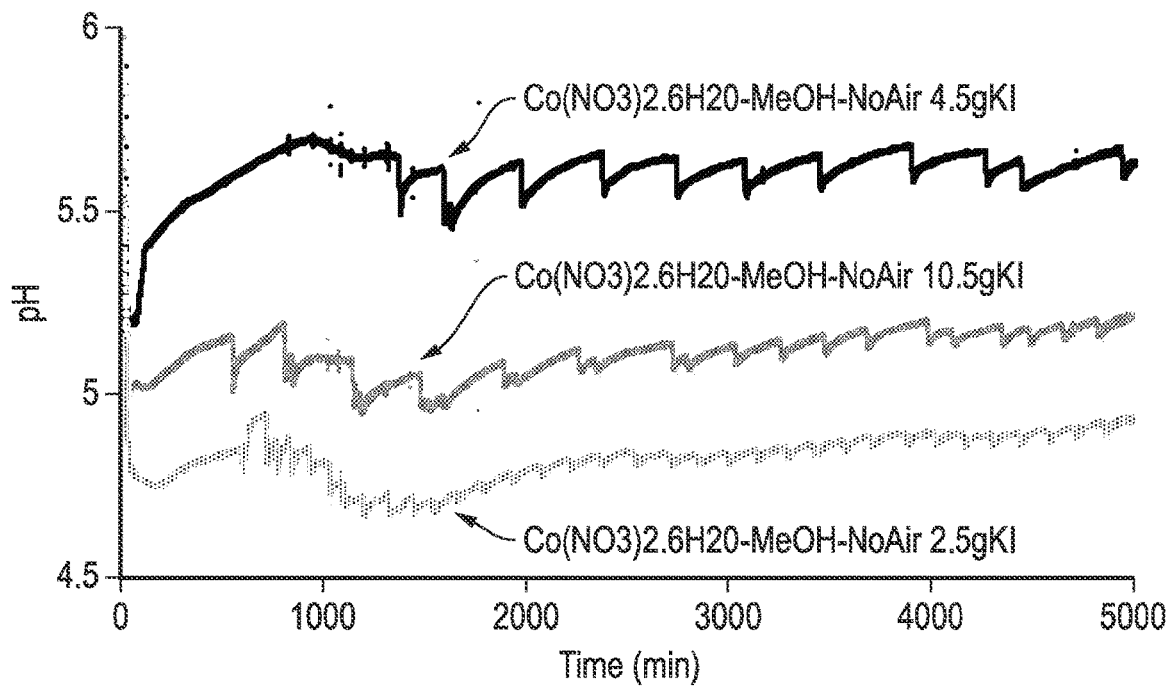
FIG. 14 shows pH recorded in the $Co(NO_3)_2 \cdot 6H_2O$ catalysed carbonylation of phenylacetylene in methanol. KI (2.5, 4.5 and 10.5 g) and catalyst are dissolved in MeOH and purging with CO (15 mL/min) started before substrate (phenylacetylene) is added. Reactions were conducted in the absence of externally brought air.

Polymeric polyacrylate-Pd is employed in PCOC, using phenylacetylene (PhAc) as a substrate and MeOH as a solvent (FIG. 10), where polyacrylate-Pd is synthesised according to S. U. Rehman, F. A. Khwaja, A. Ul Haq, M. S. Zafar, Polym. Degrad. Stab. 45 (1994) 267-272. In polymeric polyacrylate-Pd, the molecules of palladium serve as crosslinkers between the polymer chains, and polyacrylate as a counter ion, rather than as a ligand to support palladium. This construct allows a high loading of palladium to be achieved (16.26% as determined by ICP-OES) and zero leaching of palladium from the catalyst (as determined by ICP-OES, after the reaction).

In the polyacrylate-Pd-catalysed system, an initial pH drop is recorded while the KI/catalyst mixture is purged with CO. A further pH drop is observed after addition of the PhAc substrate. This pH drop then recovers from 5.05 to 5.59 and the pH oscillations start, 206 min after addition of PhAc. The oscillations occurring at this high pH are rarely observed. It is worth noting that in the case of polyacrylate-Pd, the recorded oscillations have a period of 18-24 min and a small amplitude of 0.1-0.15 pH units. After 4000 min, the starting material conversion is only 6.95%, indicating that conversion catalysis in this reaction is extremely slow and the oscillations have a potential to sustain for much longer than observed 4000 min, would such observations not be limited by the software, hardware and other equipment (i.e. gas lines not clogged).

The polyacrylate-Pd-catalysed system is further employed in PCOC using phenylacetylene as the substrate in a broad range of aliphatic alcohol solvents, in particular: MeOH, EtOH, 1-PrOH, 1-BuOH and 1-HexOH. Oscillations in pH are observed in each of the aliphatic alcohol solvents.

In MeOH, oscillations commence around 500 min into the reactions and have a bursting trend. The busts of oscillations are initially approximately 300 min apart, with the gap between them shortening and disappearing over time. In EtOH, the oscillations start promptly upon the initial drop in pH and are mixed-mode in nature. During the run in EtOH, the amplitude of the oscillations changes and a set of larger amplitude mixed-mode oscillations occur between 2600 and 4100 min. The amplitudes of the pH oscillations in both MeOH and EtOH range from very small to approximately 1 pH unit. Periods of oscillations in MeOH range from approximately 10 to 60 min, while in EtOH periods range from approximately 14 to 83 min. PhAc conversion is 37% in MeOH and 40% in EtOH.

In 1-PrOH, 1-BuOH and 1-HexOH, oscillations commence promptly at the very end of the initial pH fall. The initial pH fall is largest in 1-HexOH, followed by 1-BuOH and 1-PrOH, potentially suggesting that the longer the aliphatic chain of the alcohol, the faster the initial autocatalytic rate of pH drop when using Pd-polyacrylate. While in all three alcohols the oscillations have small amplitudes (below 0.5 pH units), their shape is very different. In 1-PrOH, oscillations initially have a "square" shape, followed by a noisy section (1220 to 1700 min). In 1-BuOH, the oscillations are mixed-mode from their onset, with amplitude increasing towards the end. In 1-HexOH, oscillations are more irregular. Periods range from 20 to 263 min in 1-PrOH, 13 to 44 min in 1-BuOH and 31 to 156 min in 1-HexOH. PhAc conversion is 37% in 1-PrOH and 34% in 1-BuOH. PhAc conversion in 1-HexOH was not possible due to co-elution of the peaks.

The polyacrylate-Pd-catalysed system is further employed in PCOC using a polymeric substrate of pegylated alkyne (PEGA) and EtOH as both reactant and solvent. Following addition of PEGA, there is an initial pH fall and an oscillatory pH trend commences. Faster pH recovery upon initial autocatalytic pH fall occurs with smaller quantities of PEGA substrate.

Thus, the PEGA/Pd-polyacrylate combination of substrate and catalyst in ethanol shows promise for future exploration in all-polymeric self-oscillating systems. Replacing the commonly used methanol with ethanol is of significance in moving towards more biocompatible oscillatory reaction systems, while using polymers as both substrates and catalyst removes the formation of small products along with the issue of leaching from prospective oscillatory materials.

Example 5—Polymer-Bound P-Cat Palladium

Polymer-bound di(acetato)dicyclohexylphenylphosphinepalldium(II) (P-cat) is a commercially available palladium catalyst. The content of Pd in P-cat is ~5%. P-cat is cross-linked and insoluble in saturated KI solution in methanol, thus providing an insight into the possibility of heterogeneous catalysis in the PCOC reaction.

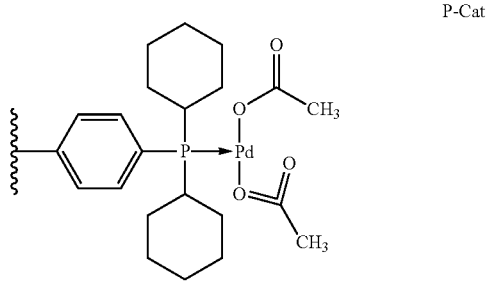

P-Cat

P-cat is employed in the PCOC reaction with constant pH monitoring, using phenylacetylene (PhAc) as a substrate and MeOH as a solvent. The changes in pH were monitored over 4000 minutes. Samples are taken at the end of the experimental runs and analysed for starting material conversion via GC-MS. In the P-cat catalysed reaction, no oscillations are observed. A small pH drop from 7.1 to 6.9 occurs initially upon CO/air purging and, after the addition of substrate, pH decreases gradually to 6.1 where it plateaus. Thus, the pH does not reach the values where oscillations typically occur in oscillatory carbonylation reactions. After 4000 min, the substrate conversion is only 3.5%.

The P-cat is further employed in the PCOC reaction where pH is artificially decreased by the addition of HI after the addition of the substrate. In this reaction, the pH decreases gradually from around 4.3 to 3.2 over 2500 min following addition of the phenylacetylene substrate and HI. After this point, a sharp drop in pH from 3.2 to 2.4 occurs followed by a gradual recovery to 2.5. Oscillations begin after 4000 min. The oscillatory pattern is complex with progressively increasing amplitude and period. The large period of the oscillation is over 330 min to 348 min, while the shorter period is 20 min to 53 min. After 4000 min, the substrate conversion is 29.5%.

Thus, the addition of HI not only helps to achieve oscillations in P-Cat but also dramatically increases phenylacetylene conversion. Moreover, after the addition of HI, P-cat demonstrates mixed-mode oscillations. This property of highly acidic HI to initiate oscillations when using a P-cat system that would not otherwise give rise to oscillations is a promising feature for targeted pH-mediated drug delivery and release.

Example 6—Cobalt Catalysed Carbonylation Reactions

Oscillations in pH have also been achieved in cobalt catalysed carbonylation reactions. A catalyst Cobalt(II) Nitrate Hexahydrate $Co(NO_3)_2 \cdot 6H_2O$ is employed using phenylacetylene as substrate and r MeOH as solvent. Oscillations in pH occur in the absence of externally brought air, thus demonstrating additional versatility of this carbonylation reaction.

Carbonylation catalysed by $Co(NO_3)_2 \cdot 6H_2O$: KI (2.5, 4.5 or 10.5 g) is dissolved in 100 mL of MeOH. $Co(NO_3)_2 \cdot 6H_2O$ (66 mg) is added and the solution stirred for 10 min. The reaction mixture is then purged with CO (15 mL/min). After 10 min, phenylacetylene (1.38 mL) substrate is added to the reaction mixture. The system is monitored for changes in pH over time.

The invention claimed is:

1. A gel that undergoes oscillatory expansion and optionally contraction; said gel comprising:
    a polymeric solid phase that expands or contracts in response to a non-physical stimulus;
    a transition metal catalyst bound to a component of the polymeric solid phase; and
    an organic compound comprising an alkyne bound to a polymer;
    wherein the catalyst catalyses an oscillatory oxidative carbonylation reaction of the organic compound, said oscillatory oxidative carbonylation reaction providing said non-physical stimulus to the gel and causing the gel to undergo oscillatory expansion and optionally contraction; and
    wherein the oscillatory oxidative carbonylation reaction is sustained without any further catalyst being added.

2. The gel of claim 1, wherein the organic compound is bound to a component of the polymeric solid phase.

3. The gel of claim 1, wherein the organic compound is present in the liquid phase of the gel.

4. The gel of claim 1, wherein the transition metal catalyst comprises palladium.

5. The gel of claim 1, wherein the transition metal catalyst comprises cobalt.

6. The gel of claim 1, wherein the polymeric solid phase is biocompatible.

7. The gel of claim 1, wherein the liquid phase of the gel comprises water.

8. The gel of claim 1, wherein the non-physical stimulus is a change in pH.

9. The gel of claim 1, wherein the non-physical stimulus is a change in temperature.

10. The gel of claim 1, wherein the non-physical stimulus is a change in redox potential.

11. The gel of claim 1, wherein the oscillatory reaction is sustained for longer than 1 hour.

12. The gel of claim 1, wherein the oscillatory reaction is a palladium-catalysed oxidative carbonylation (PCOC) reaction or a cobalt catalysed oxidative carbonylation.

13. The gel of claim 1, wherein the gel undergoes oscillatory stepwise expansion.

14. The gel of claim 1, wherein the gel undergoes oscillatory expansion and contraction.

15. The gel of claim 1, wherein the oscillatory expansion of the gel causes oscillatory release of an agent from the gel.

16. The gel of claim 15, wherein the gel further comprises the agent.

17. The gel of claim 16, wherein the gel encapsulates a reservoir within which the agent is retained.

18. The gel of claim 17, wherein one or more further reactants in the oscillatory reaction are also present in the reservoir.

19. A method of causing oscillatory expansion and contraction of a gel, the method comprising either A) providing a gel of claim 1 with one or more chemicals that react with the organic compound in the oscillatory oxidative carbonylation reaction catalysed by the catalyst and/or an initiator; or B) providing a gel of claim 1 but not comprising the organic compound, with the organic compound and optionally one or more chemicals that react with the organic compound in the oscillatory oxidative carbonylation reaction catalysed by the catalyst and/or an initiator.

20. A method of causing oscillatory release of an agent from a gel, the method comprising either A) providing a gel of claim 15 with one or more chemicals that react with the organic compound in the oscillatory oxidative carbonylation reaction catalysed by the catalyst and/or an initiator; or B) providing a gel of claim 15 but not comprising the organic compound, with the organic compound and optionally one or more chemicals that react with the compound molecule in the oscillatory oxidative carbonylation reaction catalysed by the catalyst and/or an initiator.

21. The method of claim 19 that does not comprise the addition of further catalyst or organic compound to the gel.

22. The method of claim 20 that does not comprise the addition of further catalyst or organic compound to the gel.

23. The gel of claim 1, wherein the polymeric solid phase comprises a gel-forming polymer and the alkyne is bound to the gel-forming polymer.

24. The gel of claim 1, wherein the polymeric solid phase comprises a gel-forming polymer and the alkyne is bound to a polymer interspersed within the gel-forming polymer.

* * * * *